(12) United States Patent
Rapaport

(10) Patent No.: US 8,658,763 B2
(45) Date of Patent: Feb. 25, 2014

(54) AMPHIPHILIC PEPTIDES AND HYDROGEL MATRICES THEREOF FOR BONE REPAIR

(75) Inventor: Hanna Rapaport, Lehavim (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 918 days.

(21) Appl. No.: 12/305,588

(22) PCT Filed: Jun. 19, 2007

(86) PCT No.: PCT/IL2007/000743
§ 371 (c)(1),
(2), (4) Date: Aug. 11, 2009

(87) PCT Pub. No.: WO2007/148334
PCT Pub. Date: Dec. 27, 2007

(65) Prior Publication Data
US 2010/0015197 A1  Jan. 21, 2010

Related U.S. Application Data

(60) Provisional application No. 60/814,880, filed on Jun. 20, 2006.

(51) Int. Cl.
| | |
|---|---|
| A61K 38/04 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| A61K 38/00 | (2006.01) |
| A61K 51/00 | (2006.01) |

(52) U.S. Cl.
USPC ............ 530/327; 530/333; 530/300; 514/1.1; 424/1.69

(58) Field of Classification Search
None
See application file for complete search history.

(56) References Cited

U.S. PATENT DOCUMENTS

| | | | | |
|---|---|---|---|---|
| 4,792,525 | A | 12/1988 | Ruoslahti et al. | 435/240.243 |
| 4,988,621 | A | 1/1991 | Ruoslahti et al. | 435/240.2 |
| 5,670,483 | A | 9/1997 | Zhang et al. | 514/14 |
| 5,695,997 | A | 12/1997 | Ruoslahti et al. | 435/375 |
| 5,955,343 | A | 9/1999 | Holmes et al. | 435/240.1 |
| 6,291,428 | B1 | 9/2001 | Macaulay et al. | 514/12 |
| 6,492,525 | B1 | 12/2002 | Bertrand et al. | 558/101 |
| 6,548,630 | B1 | 4/2003 | Zhang et al. | 530/300 |
| 6,800,481 | B1 | 10/2004 | Holmes et al. | 435/401 |
| 7,163,920 | B2 | 1/2007 | Dhanaraj et al. | 514/15 |
| 2005/0181973 | A1 | 8/2005 | Genove et al. | 514/2 |
| 2006/0025524 | A1 | 2/2006 | Schneider et al. | 525/54.1 |
| 2006/0154852 | A1 | 7/2006 | Boden | |
| 2010/0297096 | A1* | 11/2010 | Rapaport | 424/94.1 |

FOREIGN PATENT DOCUMENTS

| | | |
|---|---|---|
| JP | 6-192290 A | 7/1994 |
| JP | 2007105186 A | 4/2007 |
| WO | WO 2005/003292 A2 | 1/2005 |
| WO | WO 2006/014570 A2 | 2/2006 |

OTHER PUBLICATIONS

Database Geneseq [online] Mar. 21, 1995 "Peptide for treating diseases related to anti-DNA antibodies" XP002455844 retrieved from EBI accession No. GSP:AAR57394 Databaseaccession No. AAR57394 abstract.*
Database Geneseq [online] Mar. 21, 1995 "peptide for treating diseases related to anti-DNA antibodies" XP002455845 retrieved from EBI accession No. GSP:AAR57393 Databaseaccession No. AAR57393 abstract.*
Rapaport et al. Two-Dimensional Order in b-Sheet Peptide Monolayers. Journal of the American Chemical Society (2000), 122(50), 12523-12529 (which discloses Applicant's described but not claimed peptide SEQ ID No. 23).*
International Search Report PCT/IL2007/000743 Dated Nov. 6, 2007.
Addadi, L. and Weiner, S. (1985) Interactions between acidic proteins and crystals: stereochemical requirements in biomineralization. *Proc Natl Acad Sci USA* 82(12):4110-4114.
Bolander, Mark E. (1992) Regulation of fracture repair by growth factors. *Proc Soc Exp Biol Med* 200(2):165-170.
Boskey, Adele L. (1998) Biomineralization: conflicts, challenges, and opportunities. *J Cell Biochem Suppl* 30-31:83-91.
Caplan, M. R. et al., (2000) Self-assembly of a beta-sheet protein governed by relief of electrostatic repulsion relative to van der Weals attraction. *Biomacromolecules* 1(4):627-631.
Collier, Joel H. and Messersmith, Phillip B. (2003) Enzymatic modification of self-assembled peptide structures with tissue transglutaminase. *Bioconjugate Chem* 14(4):748-755.
Colombier, M. L. et al., (1999) A Single Low Dose of RGTA®, a New Healing Agent, Hastens Wound Maturation and Enhances Bone Deposition in Rat Craniotomy Defects. *Cells Tissues Organs* 164(3):131-140.
DeGrado, W. F. and Lear, J. D. (1985) Induction of peptide conformation at apolar water interfaces. 1. A study with model peptides of defined hydrophobic periodicity. *J Am Chem Soc* 107(25):7684-7689.
DeLange, G. L. and Donath, K. (1989) Interface between bone tissue and implants of solid hydroxyapatite or hydroxyapatite-coated titanium implants. *Biomaterials* 10(2):121-125.

(Continued)

*Primary Examiner* — Maury Audet
(74) *Attorney, Agent, or Firm* — Winston & Strawn LLP

(57) ABSTRACT

The present invention relates to the field of tissue engineering and more specifically to amphiphilic peptides and peptide matrices thereof useful in vitro and in situ biomineralization and inducing bone repair. The present invention provides peptides, which are useful in hydrogels and other pharmaceutical compositions, and methods and kits of use for bone repair and promotion of biomineralization. Certain hydrogels according to the invention comprise cells within or adhered to the peptide matrix.

14 Claims, 10 Drawing Sheets

(56) References Cited

OTHER PUBLICATIONS

Ganss, B. et al., (1999) Bone sialoprotein. *Crit Rev Oral Biol Med* 10(1):79-98.

Gilbert, Michele et al., (2000) Chimeric peptides of statherin and osteopontin that bind hydroxyapatite and mediate cell adhesion. *J Biol Chem* 275(21):16213-16218.

Goldberg, H. A. et al., (2001) Binding of bone sialoprotein, osteopontin and synthetic polypeptides to hydroxyapatite. *Connect Tissue Res* 42(1):25-37.

He, Gen et al., (2005) Spatially and temporally controlled biomineralization is facilitated by interaction between self-assembled dentin matrix protein 1 and calcium phosphate nuclei in solution. *Biochemistry* 44(49):16140-16148.

Hollinger, Jeffrey O. and Kleinschmidt, James C. (1990) The Critical Size Defect as an Experimental Model to Test Bone Repair Materials. *J Craniofacial Surg* 1(1):60-68.

Hunter, Graeme K. et al., (1996) Nucleation and inhibition of hydroxyapatite formation by mineralized tissue proteins. *Biochem J* 317(1):59-64.

Hunziker, E. B. (2001) Articular cartilage repair: basic science and clinical progress. A review of the current status and prospects. *Osteoart Cart* 10(6):432-463.

Iijima, Mayumi et al., (1998) Effects of Ca addition on the formation of octacalcium phosphate and apatite in solution at pH 7.4 and at 37° C. *Journal of Crystal Growth* 193(1-2):182-188.

Koh, Chester J. and Atala, Anthony (2004) Tissue Engineering, Stem Cells, and Cloning: Opportunities for Regenerative Medicine. *J Am Soc Nephrol* 15(5):1113-1125.

Kokubo, T. et al., (1990) Solutions able to reproduce in vivo surface-structure changes in bioactive glass-ceramic A-W$^3$. *J Biomed Mater Res* 24(6):721-34.

LeGeros, Racquel Zapanta (2002) Properties of osteoconductive biomaterials: calcium phosphates. *Clin Orthop Relat Res* 395:81-98.

Mann, Stephen (1988) Molecular recognition in biomineralization. *Nature* 332(6160):119-124.

Oldberg, Ake et al., (1988) The primary structure of a cell binding bone sialoprotein. *J Biol Chem* 263(36):19430-19432.

Oliveira, A. L. et al., (2003) Nature-inspired calcium phosphate coatings: present status and novel advances in the science of mimicry. *Current Opinion in Solid State & Materials Science* 7(4-5):309-318.

Ou-Yang, H. et al., (2000) Two-Dimensional Vibrational Correlation Spectroscopy of In Vitro Hydroxyapatite Maturation. *Biopolymers (Biospectroscopy)* 57:129-139.

Ozbas, Bulent et al., (2004) Characterization of semiflexible fibril networks formed via intramolecular folding and self assembly of amphiphilic B-hairpin molecules. *Abstracts of Papers American Chemical Society* 228(2):U374-U375.

Ramachandran, Sivakumar et al., (2005) Repeated rapid shear-responsiveness of peptide hydrogels with tunable shear modulus. *Biomacromolecules* 6(3):1316-1321.

Rapaport, Hana et al., (2000) Two dimentional order in beta-sheet peptide monolayer. *J Am Chem Soc* 122(50):12523-12529.

Rapaport, Hanna et al., (2002) Assembly of triple-stranded β-sheet peptides at interfaces. *J Am Chem Soc* 124(32):9342-9343.

Segman-Magidovich, Shlomit et al., (2008) Matrices of Acidic *b*-Sheet Peptides as Templates for Calcium Phosphate Mineralization. *Adv Mater* 20(11):2156-2161.

Traub, Wolfie et al., (1989) Three-dimensional ordered distribution of crystals in turkey tendon collagen fibers. *Proc Natl Aced Sci USA* 86(24):9822-9826.

Valentin, Andreas H. and Weber, J. (2004) Receptor technology-cell binding to P-15: a new method of regenerating bone quickly and safely—preliminary histomorphometrical and mechanical results in sinus floor augmentations. *Keio J Med* 53(3):166-171.

Weiner, Stephen and Addadi, Lia (1997) Design strategies in mineralized biological materials. *J Mater Chem* 7(5):689-702.

Young, Marian F. et al., (1992) Structure, expression and regulation of the major noncollagenous matrix proteins of bone. *Clin Orthop Relat Res* 281:275-294.

Zhang, Shuguang et al., (1993) Spontaneous assembly of a self-complemetary oligopeptide to form a stable macroscopic membrane. *Proc Natl Aced Sci USA* 90(8):3334-3338.

Database Geneseq [online] Mar. 21, 1995 "peptide for treating diseases related to anti-DNA antibodies" XP002455844 retrieved from EBI accession No. GSP:AAR57394 Database accession No. AAR57394 abstract.

Database Geneseq [online] Mar. 21, 1995 "Peptide for treating diseases related to anti-DNA antibodies" XP002455845 retrieved from EBI accession No. GSP:AAR57393 Database accession No. AAR57393 abstract.

Geneseq database accession No. AAM95164 WO 2001/55320, 2001.

Holmes et al., Extensive neurite outgrowth and active synapse formation on self-assembling peptide scaffolds. Proc Natl Aced Sci USA 97(12): 6728-6733 (2000).

Isenberg et al., Elasticity of crystalline beta-sheet monolayers. J Am Chem Soc 128(38): 12468-12472 (2006).

Jayawarna et al., Nanostructured Hydrogels for Three-Dimensional Cell Culture Through Self-Assembly of Fluorenylmethoxycarbonyl-Dipeptides. Adv Mater 18(5); 611-614 (2006).

Zhang, Fabrication of novel biomaterials through molecular self-assembly, Nat Biotechnol 21(10): 1171-1178 (2003).

Database WPI week 200736 Thomson Scientific, London, GB; AN 2007-382871 XP002528834 & JP 2007105186.

* cited by examiner

Figure 1A
Figure 1B
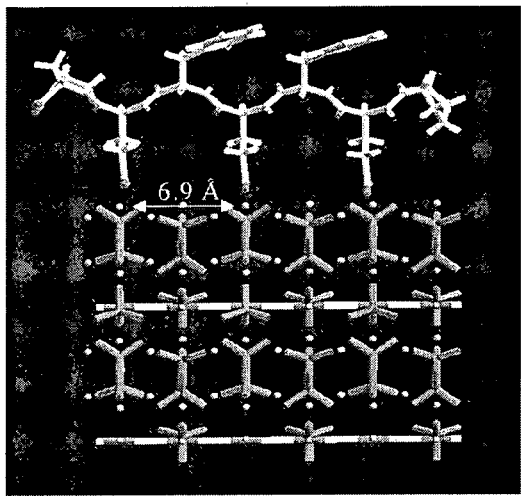 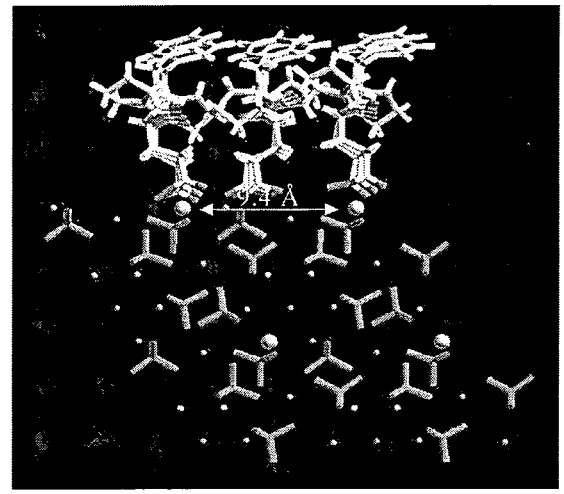

Figure 6A  Figure 6B  Figure 6C
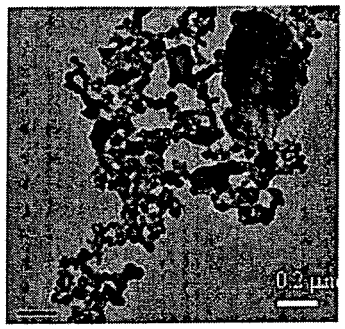 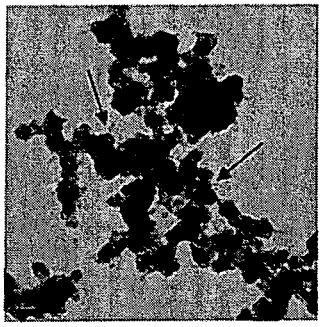 
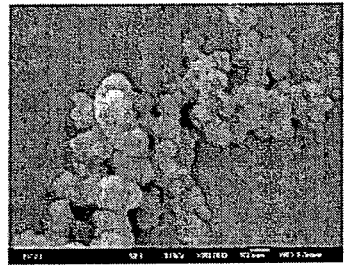 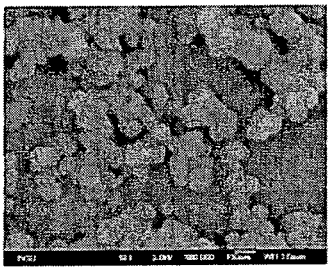
Figure 6D  Figure 6E Figure 8A  
Cover slip
Figure 8B  
$P_{FD}$-13
Figure 8C  
$P_{FE}$-13
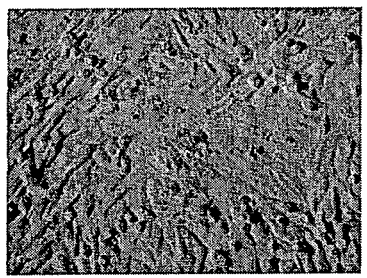
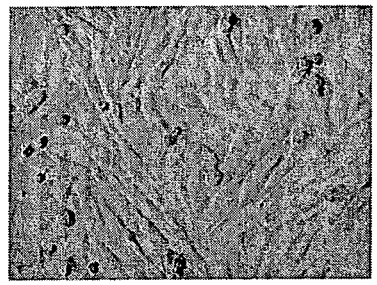
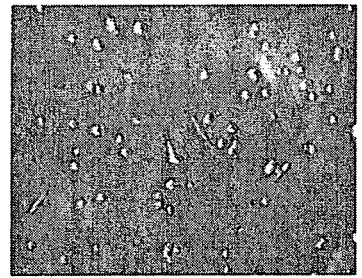
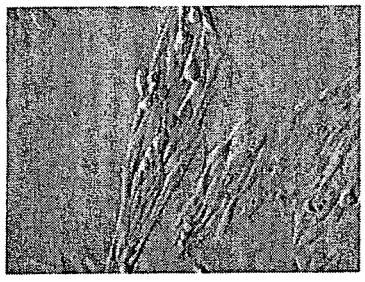
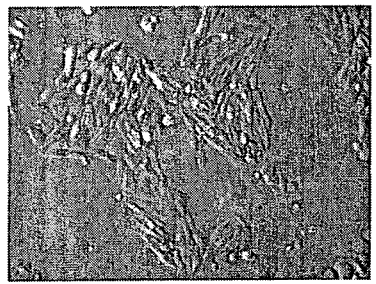
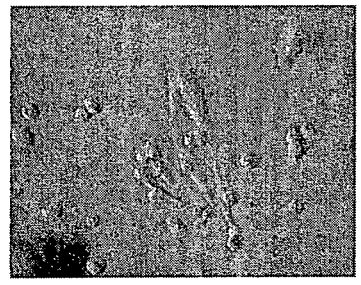
Figure 8D
Figure 8E
Figure 8F

AMPHIPHILIC PEPTIDES AND HYDROGEL MATRICES THEREOF FOR BONE REPAIR

This application is a 371 filing of International Patent Application PCT/IL2007/000743 filed Jun. 19, 2007, which claims the benefit of application No. 60/814,880 filed Jun. 20, 2006.

FIELD OF THE INVENTION

The present invention relates in general to the field of tissue engineering and more specifically to amphiphilic peptides and hydrogel matrices formed by these peptides useful for in vitro and in situ mineralization and for inducing bone repair.

BACKGROUND OF THE INVENTION

Tissue engineering may be defined as the art of reconstructing mammalian tissues, both structurally and functionally (Hunziker, 2002). Tissue engineering includes the provision of cells or of a natural or synthetic scaffold that serves as an architectural support onto which cells may attach, proliferate, and synthesize new tissue to replace tissue losses due to disease, trauma or age.

The trend in tissue engineering in general is to utilize biomaterials to promote controlled healing or tissue regeneration. In orthopedics and dentistry the clinical focus transforms from traditional metal and other inorganic implants, plates, screws and cements to biologically based products for mineralized tissue regeneration.

Natural polymers are of major interest in tissue engineering since they tend to be biocompatible and biodegradable and may have the potential to enhance cell adhesion and proliferation. Additionally, such material substrates can be prepared in various forms and shapes, including strips, sheets, sponges and beads for implantation.

Bone

Bone is a unique type of tissue that comprises both organic and inorganic phases, that undergoes modeling and remodeling wherein old bone is lost (resorption) and new bone is formed (formation/replacement). Bone formation may be enhanced either by recruiting osteoblasts, the bone forming cells, or by inhibiting recruitment or activity of osteoclasts, the bone resorbing cells. Osteoblasts and osteoclasts work together in a coordinated fashion to form and remodel bone tissue. Bone repair or replacement is a viable consideration in indications including osteopenia, osteoporosis, bone tumors, spinal fusion and fractures.

Biomineralization of Bone

Biomineralization refers to the deposition of inorganic solids in biological systems. Mann (2001) has defined the term biologically controlled mineralization as the highly regulated process that produces materials such as bones, shells and teeth that have specific biological functions and structures. Biologically controlled mineralization is characterized by specific crystalline and chemical properties, which may include: rather uniform particles size, well-defined structures and compositions, high level of spatial organization, preferred crystallographic orientation and higher order assembly into hierarchical structures.

Hydroxyapatite (HA), having the chemical formula $Ca_{10}(PO4)_6(OH)_2$, is one of the major constituents of the inorganic components in bone, as well as in other human hard tissues (Posner, 1969; Mann, 2001). HA enables formation of bone on its surface by supporting attachment, migration, proliferation, and differentiation of bone forming cells (Oliveira, 2003; Delange, 1989). The mechanical properties of HA in absence of the organic matrix onto which it deposits in vivo, does not resemble natural human bone. HA is rigid and often very brittle and thus cannot be used per se for weight-bearing applications (Oliveira, 2003).

The natural mineralization of bone is considered to occur by deposition of HA or its precursor forms in an organic extracellular matrix composed of collagen and other proteins, many of which are rich in acidic residues (Hunter, 1996; Teraub, 1989). The major role of collagen is to render the bone improved mechanical properties through an hierarchical composition of the organic fibers and aligned HA minerals (Lowenstam et al., 1989, Mann, S., 2001, Teraub 1989). Non-collagenous proteins isolated from bone extracellular matrices that are rich in acidic amino acids i.e. bone sialoprotein, osteopontin, osteocalcin, osteonectin and others (Young et al, 1992), have been proposed to be involved in the nucleation, and growth of carbonated apatite (Hunter et al., 1996). Among these, sialoprotein (BSP), a glycosylated and sulphated phosphoprotein, found almost exclusively in mineralized connective tissues, is the most widely accepted protein linked to apatite nucleation (Ganss et al., 1999). BSP exhibits fragments rich in both glutamic- and aspartic-acid residues (Oldberg et al, 1988) as well as the cell binding arginine-glycine-aspartate (RGD) motifs. Despite numerous studies aiming at unraveling the principles of apatite biomineralization, detailed mechanisms that account for the role of acid rich proteins in this process, are yet to be elucidated.

Among the main properties of organic interfaces that may be contributing to nucleation of biominerals are electrostatic accumulation and structural correspondence. Electrostatic accumulation is considered to be the initial step in biomineralization. It is believed that one of the most essential properties of bone acid-rich proteins and possibly also collagen is their ability to control nucleation by charged amino acid residues on their surfaces. The primary residues are acidic and phosphorylated amino acids, which at biological pH, may expose charged functional groups, i.e. negatively charged carboxylate groups of glutamic acid and aspartic acid as well as negatively charged phosphates. (Addadi, 1985; Mann, 1988).

Many materials have been utilized for bone repair. Synthetic materials are being developed in order to replace autologous harvesting problems and the health risks attendant with allogeneic material. Inorganic materials such as calcium phosphate and hydroxyapatite have been utilized as bone and dental fillers (reviewed in LeGeros, 2002) but lacking many of the extra cellular like functionalities, none can be considered entirely satisfactory in meeting the criteria required for successful tissue engineering.

Recent developments in the study of peptide self-assembly matrices have advanced the understanding of the relationship between amino acid composition, molecular assembly forms and interaction of these materials with cells. Certain peptides and proteins have been shown to promote osteogenic cell adhesion. A 15-mer peptide fragment of collagen 1α1 has been designed to include cell binding domain for mesenchymal progenitor cells. This fragment is commercially available as Pepgen P-15® in combination with an organic bovine derived bone matrix (ABM) as particles or cement for bone grafting in patients with periodontal osseous defects (Valentin and Weber, 2004). Gilbert, et al. (2000) teach a fusion peptide of two extracellular matrix proteins, statherin and osteopontin that binds hydroxyapatite and mediates cell adhesion. The chimeric peptide was shown to have utility in tissue engineering and vaccine applications.

Goldberg, et al. (2001) teach synthetic poly-L-glutamic acid and poly-L-aspartic acid peptides and their ability to bind hydroxyapatite. He, et al. (2003) report that the acidic protein dentin matrix protein 1 (DMP 1) assembles into acidic clusters that are claimed to nucleate the formation of hydroxyapatite in vitro.

International patent application WO 2005/003292 relates to a composition useful for making homogenously mineralized self-assembled peptide amphiphile nanofibers and nanofiber gels. The peptide amphiphiles comprise three regions: an alkyl tail at the N-terminus providing the peptide with a hydrophobic nature, a tetra cysteine region, and a C-terminal sequence which includes cell adhesion or crystal nucleation sequences. Due to their amphiphilic nature the peptides self assemble into nanofiber matrices which may be prepared with appropriate phosphate and calcium solutions to yield mineral templated matrices.

U.S. Pat. Nos. 5,670,483; 5,955,343; 6,548,630 and 6,800,481 relate to amphiphilic peptides having alternating hydrophobic and hydrophilic residues, and their resultant macroscopic membranes, respectively. Specifically, two peptides having the amino acid sequences $(AEAEAKAK)_2$ and $(ARARADAD)_2$ were shown to self assemble into macroscopic membranes useful for in vitro culturing of cells and biomaterial applications. The former sequence was originally found in a region of alternating hydrophobic and hydrophilic residues in a yeast protein called zuotin.

US Patent Publication No. US 2005/0181973 discloses a self-assembling peptide comprising two domains, the first one comprising complementary alternating hydrophobic and hydrophilic amino acids that are overall are neutrally charged with equal number of positively and negatively charged amino acids, that self-assemble into a macroscopic structure, including hydrogels, when present in unmodified form; and a second amino acid domain comprising a biologically active peptide motif or a target site for an interaction with a biomolecule. That application further teaches that replacement of the positively charged residues, lysine (K) and arginine (R), by negatively charged residues, such as aspartate (D) and glutamate (E), prevents peptide self-assembly into macroscopic structures and only β-sheet and not macroscopic structures are formed in the presence of salt. The VE20 peptide, a 20-mer peptide comprising alternating valine (V) and glutamate (E) amino acids, was disclosed as not able to self-assemble to form macroscopic structures.

US Patent Publication No. US 2006/0025524 discloses a method for making a hydrogel from a solution of peptides, mainly peptides containing Val-Lys repeats or peptides with at least one positively-charged residue per 6 amino acids, which undergo change in conformation from random coil to β-hairpin secondary structures, that promote hydrogel formation. The hydrogel is formed by alteration peptide concentration or one or more environmental signals or stimuli (e.g., change in pH, ionic strength, specific ion concentration, and/or temperature of the solution).

The "RGD" (Arg-Gly-Asp) tri-peptide sequence, which occurs in fibronectin and has been shown to promote cell adhesion and growth, has been disclosed in inter alia, U.S. Pat. Nos. 4,988,621; 4,792,525 and 5,695,997. U.S. Pat. No. 6,291,428 teaches peptides comprising the RGD amino acid sequence for promoting in situ bone mineralization.

The inventor of the present invention reported amphiphilic peptides that form β-strand monolayers when spread at air-water interfaces (Rapaport, 2000; Rapaport, 2002). Peptides of seven to 17 amino acid residues were found to form crystalline arrays with coherence lengths of about 100 to about 1000 Å. A 30-residue peptide, which incorporates proline residues to induce reverse turns, was designed to form an ordered triple stranded β-sheet monolayer at the air water interface. The formation of hydrogels from these peptides was neither taught nor suggested in those publications.

There is an unmet medical need for multifunctional biomaterials which may be fabricated in various clinically relevant forms such as hydrogels, membranes or solid matrices and mineral-peptide composites, useful for promoting both osteogenic cell activity and biomineralization, in situ.

SUMMARY OF THE INVENTION

The present invention provides amphiphilic peptides comprising predominantly acidic amino acids, which are capable, alone or in combination with ions and minerals, of forming hydrogels at physiological pH and serving as scaffolds for mineralization.

It is now disclosed in accordance with the present invention that certain amphiphilic peptides comprising alternating hydrophobic and hydrophilic residues, wherein the hydrophilic residues are predominantly acidic, self-assemble into three dimensional structures within aqueous solution, and form hydrogel fibrous matrices with β-sheet fibers acting as scaffolds for mineralization. The hydrogels may serve to promote mineralization in vitro, ex vivo, in vivo or in situ. The peptide hydrogels may serve as a depot for bioactive agents including active proteins, growth factors, hormones, antibiotics and bone anti-resorptive agents. The peptide matrices are modular structures onto which various functionalities may be tailored, including osteoinduction, osteogenic cell attachment, and strong chemical bonding to metal implants.

The present invention is based in part on the finding that there is a structural correlation between peptides in the β-sheet conformation and the hydroxyapatite structure. Without wishing to be bound to any theory or mechanism of action it is postulated that the β-sheet structure of the peptides in the hydrogel thus serves as a nucleation center for calcified mineralization.

Peptide matrices and hydrogels comprising amphiphilic peptides of the present invention serve as a template or nucleation center for in vitro and in situ biomineralization, to mimic the formation of natural bone tissue thereby providing rapid bone regeneration, implant-bone integration and a shortened recovery period.

According to one aspect the invention provides a hydrogel composition comprising at least one amphiphilic peptide comprising at least 2 dyads of alternating hydrophobic/hydrophilic amino acid residues, or a derivative or a salt thereof, capable of forming a β-sheet structure and promoting biomineralization, wherein the peptide comprises:

i. 2-20 pairs of hydrophobic-hydrophilic alternating amino acid residues wherein the hydrophilic amino acid side chain is selected from the group consisting of: a negatively charged amino acid, a hydroxyl-containing amino acid, and a phosphorylated-hydroxyl-containing amino acid; and ii. no more than 10% positively charged amino acid residues; and an aqueous medium in which the peptide is dissolved.

According to some embodiments the at least one amphiphilic peptide is 4-40 amino acids in length. According to some embodiments the at least one amphiphilic peptide is 7-28 amino acids in length. According to some embodiments the peptide further comprises at least one terminal Pro residue. According to certain embodiments the peptide further comprises two terminal Pro residues. According to one embodiment the hydrophobic amino acid is selected from the group consisting of Phe, Leu, Ile, Val and Ala. According to certain embodiments the hydrophobic amino acid is Phe or Leu. According to some embodiments the hydrophilic amino acid is selected from the group consisting of Glu, Asp, Tyr, Ser, Thr, Ser(PO$_4$), Thr(PO$_4$), and Tyr(PO$_4$).

According to another embodiment, the peptide comprises an amino acid sequence according to Formula I:

$$X\text{-(hydrophobic-hydrophilic)}_n\text{-B} \quad \text{(Formula I)}$$

wherein n designates an integer of 2-20, hydrophobic designates a hydrophobic amino acid residue, hydrophilic designates a hydrophilic amino acid residue, X designates Pro, Pro-hydrophilic or represents the peptide's amino terminus, and B is Pro or represents the peptide's carboxy terminus.

According to some embodiments the amino terminus is modified, e.g., it may be acetylated. According to some embodiments the carboxy terminus is modified, e.g., it may be amidated.

According to a specific embodiment, the peptide comprises an amino acid sequence selected from the group consisting of:

X-(Phe-Glu)$_n$-B
X-(Phe-Asp)$_n$-B
X-(Leu-Glu)$_n$-B
X-(Leu-Asp)$_n$-B wherein n designates an integer of 2-20, X designates Pro, Pro-hydrophilic or represents the peptide's amino terminus, hydrophilic designates a hydrophilic amino acid residue, and B is Pro or represents the peptide's carboxy terminus.

According to some embodiments the amino terminus is modified, e.g., it may be acetylated. According to some embodiments the carboxy terminus is modified, e.g., it may be amidated.

According to one embodiment the hydrogel according to the invention comprises an amphiphilic peptide comprising a sequence selected from the group consisting of:

Pro-Glu-(Phe-Glu)$_n$ wherein n is an integer of 3-7;
Glu-(Phe-Glu)$_n$-Pro wherein n is an integer of 3-7;
Pro-(Ser-Phe)$_n$-Ser-Pro wherein n is an integer of 3-7;
Pro-(Ser-PO$_4$-Phe)$_n$-SerPO$_4$-Pro wherein n is an integer of 3-7;
Pro-(TyrPO$_4$-Phe)$_n$-TyrPO$_4$-Pro wherein n is an integer of 3-7;
Pro-(Glu-Leu)$_n$-Glu-Pro wherein n is an integer of 3-7;
Pro-(Asp-Phe)$_n$-Asp-Pro wherein n is an integer of 3-7;
Pro-(Asp-Leu)$_n$-Asp-Pro wherein n is an integer of 3-7;
Pro-(Ser-Leu)$_5$-Ser-Pro wherein n is an integer of 3-7;
Pro-(SerPO$_4$-Leu)$_n$-SerPO$_4$-Pro wherein n is an integer of 3-7;
Pro-(TyrPO$_4$-Leu)$_n$-TyrPO$_4$-Pro wherein n is an integer of 3-7;
Pro-(Glu-Phe-Ser-Phe)$_n$-Glu-Pro wherein n is an integer of 3-7;
Pro-(SerPO$_4$-Phe-Ser-Phe)$_n$-Ser-Pro wherein n is an integer of 1-4;
Pro-(SerPO$_4$-Phe-Glu-Phe)$_n$-Glu-Pro wherein n is an integer of 1-4;
Pro-(SerPO$_4$-Phe-Asp-Phe)-Asp-Pro wherein n is an integer of 1-4; and
Pro-Glu-(Phe-Glu)$_n$-(Gly)$_m$-Arg-Gly-Asp wherein n is an integer of 2-15 and m is an integer of 0-10.

According to a specific embodiment the hydrogel according to the invention comprises an amphiphilic peptide comprising a sequence selected from the group consisting of:

| | |
|---|---|
| Pro-Glu-(Phe-Glu)$_5$; | (SEQ ID NO: 1) |
| Glu-(Phe-Glu)$_5$-Pro; | (SEQ ID NO: 2) |

-continued

| | |
|---|---|
| Pro-(Ser-Phe)$_5$-Ser-Pro; | (SEQ ID NO: 3) |
| Pro-(SerPO$_4$-Phe)$_5$-SerPO$_4$-Pro; | (SEQ ID NO: 4) |
| Pro-(TyrPO$_4$-Phe)$_5$-TyrPO$_4$-Pro; | (SEQ ID NO: 5) |
| Pro-(Glu-Leu)$_5$-Glu-Pro; | (SEQ ID NO: 6) |
| Pro-(Asp-Leu)$_5$-Asp-Pro; | (SEQ ID NO: 7) |
| Pro-(Ser-Leu)$_5$-Ser-Pro; | (SEQ ID NO: 8) |
| Pro-(SerPO$_4$-Leu)$_5$-SerPO$_4$-Pro; | (SEQ ID NO: 9) |
| Pro-(TyrPO$_4$-Leu)$_5$-TyrPO$_4$-Pro; | (SEQ ID NO: 10) |
| Pro-(Glu-Phe-Ser-Phe)$_4$-Glu-Pro; | (SEQ ID NO: 11) |
| Pro-(SerPO$_4$-Phe-Ser-Phe)$_4$-Ser-Pro; | (SEQ ID NO: 12) |
| Pro-(SerPO$_4$-Phe-Glu-Phe)$_4$-Glu-Pro; | (SEQ ID NO: 13) |
| Pro-(SerPO$_4$-Phe-Asp-Phe)$_4$-Asp-Pro; | (SEQ ID NO: 14) |
| Ala-Leu-Glu-(Phe-Glu)$_3$-Pro-Ala-(Glu-Phe)$_3$-Glu-Leu-Pro-Ala-Leu-Glu-(Phe-Glu)$_3$-Pro; | (SEQ ID NO: 15) |
| Pro-Glu-(Phe-Glu)$_2$-Lys-(Glu-Phe)$_2$-Glu-Pro; | (SEQ ID NO: 16) |
| Pro-Glu-(Phe-Glu)$_5$-(Gly)$_3$-Arg-Gly-Asp-Ser; | (SEQ ID NO: 17) |
| (Phe-Glu)$_3$-Pro-(Gly)$_3$-Arg-Gly-Asp-Ser; | (SEQ ID NO: 18) |
| Ac-Pro-Asp-(Phe-Asp)$_5$-Pro-NH$_2$;; | (SEQ ID NO: 19) |
| Pro-Asp-(Phe-Asp)$_6$; and | (SEQ ID NO: 20) |
| (Phe-Asp)$_6$. | (SEQ ID NO: 21) |

Hydrogel according to the present invention refers to a three-dimensional hydrated polymeric porous matrix of bioactive nanofibers comprising amphiphilic peptides in β-sheet conformation. It is to be understood that the present invention encompass dry "hydrogel forming peptides" that will swell in aqueous environments, as well as hydrated materials.

According to specific embodiments the hydrogel comprises at least two different peptide sequences, mixed or covalently linked. According to another embodiment the hydrogel further comprises a pre-loaded mineral-salt solution or aggregates. According to a specific embodiment the hydrogel comprises a calcium phosphate mineral selected from the group consisting of amorphous calcium phosphate, tricalcium phosphate or hydroxyapatite. According to yet another embodiment the hydrogel composition comprises pre-loaded polysaccharides. According to a specific embodiment the polysaccharide is selected from the group consisting of: hyaluronic acid, alginate or a sulfated polysaccharide such as a glycosaminoglycan. According to a more specific embodiment the polysaccharide is selected from the group consisting of: chondroitin 4-sulfate, chondroitin 6-sulfate, dermatan sulfate, keratan sulfate, heparin, heparan sulfate, sucrose octasulfate, perlecan, syndecan, glypican and combinations thereof. According to a more specific embodiment the polysaccharide is alginate or hyaluronic acid. According to another specific embodiment the hydrogel comprises the peptide Ac-Pro-Asp-(Phe-Asp)$_5$-Pro and the polysaccharide alginate. According to a specific embodiment the hydrogel comprises calcified mineral powder or particulates.

According to some embodiments the hydrogel comprises a mixture of one or more peptides. In various embodiments the hydrogel further comprises at least one therapeutic agent. A therapeutic agents according to the invention includes inter alia growth factors, cytokines, chemotherapeutic drugs, enzymes, anti-microbials, anti-resorptive agents and anti-inflammatory agents.

According to another specific embodiment, the hydrogel comprises cells entrapped within or adhered to the peptide matrix.

According to yet another embodiment the hydrogel of the present invention serve as a carrier for modified release of at least one therapeutic agent, e.g. slow release, sustained release etc.

In another aspect the present invention provides an amphiphilic peptide comprising at least 2 pairs of alternating hydrophobic/hydrophilic amino acid residues, or a derivative or a salt thereof, capable of forming a β-sheet structure and promoting biomineralization, wherein the peptide comprises:

i. 2-20 pairs of hydrophobic-hydrophilic alternating amino acid residues wherein the hydrophilic amino acid side chain is selected from the group consisting of: a negatively charged amino acid, a hydroxyl-containing amino acid, and a phosphorylated-hydroxyl-containing amino acid; and ii. no more than 10% positively charged amino acid residues;

an aqueous medium in which the peptide is dissolved; and wherein the amphiphilic peptide is other than Pro-Glu-(Phe-Glu)$_{2-7}$-Pro.

It is to be explicitly understood that known peptides are excluded from the present invention.

According to some embodiments the at least one amphiphilic peptide is 4-40 amino acids in length. According to some embodiments the at least one amphiphilic peptide is 7-28 amino acids in length. According to one embodiment the peptide further comprises at least one terminal Pro residue. According to another embodiment the peptide further comprises two terminal Pro residues. According to one embodiment the hydrophobic amino acid is selected from the group consisting of Phe, Leu, Ile, Val and Ala. According to another embodiment the hydrophobic amino acid is Phe or Leu. According to yet another embodiment the hydrophilic amino acid is selected from the group consisting of: Glu, Asp, Tyr, Ser, Thr, Ser(PO$_4$), Thr(PO$_4$), and Tyr(PO$_4$).

According to another embodiment, the peptide comprises an amino acid sequence according to Formula I:

X-(hydrophobic-hydrophilic)$_n$-B    (Formula I)

wherein n designates an integer of 2-20, hydrophobic designates a hydrophobic amino acid residue, hydrophilic designates a hydrophilic amino acid residue, X designates Pro, Pro-hydrophilic or represents the peptide's amino terminus, and B is Pro or represents the peptide's carboxy terminus.

According to some embodiments the amino terminus is modified, e.g., it may be acetylated. According to some embodiments the carboxy terminus is modified, e.g., it may be amidated.

According to a specific embodiment, the peptide comprises an amino acid sequence selected from the group consisting of:
X-(Phe-Glu)$_n$-B
X-(Phe-Asp)$_n$-B
X-(Leu-Glu)$_n$-B
X-(Leu-Asp)$_n$-B wherein n designates an integer of 2-20, X designates Pro, Pro-hydrophilic or represents the peptide's amino terminus, hydrophilic designates a hydrophilic amino acid residue, and B is Pro or represents the peptide's carboxy terminus.

According to some embodiments the amino terminus is modified, e.g., it may be acetylated. According to some embodiments the carboxy terminus is modified, e.g., it may be amidated.

According to one embodiment the amphiphilic peptide of the invention comprises a sequence selected from the group consisting of:

Pro-(Ser-Phe)$_n$-Ser-Pro wherein n is an integer of 3-7;
Pro-(SerPO$_4$-Phe)$_n$-SerPO$_4$-Pro wherein n is an integer of 3-7;
Pro-(TyrPO$_4$-Phe)$_n$-TyrPO$_4$-Pro wherein n is an integer of 3-7;
Pro-(Glu-Leu)$_n$-Glu-Pro wherein n is an integer of 3-7;
Pro-(Asp-Leu)$_n$-Asp-Pro wherein n is an integer of 3-7;
Pro-(Ser-Leu)$_5$-Ser-Pro wherein n is an integer of 3-7;
Pro-(Asp-Phe)$_n$-Asp-Pro wherein n is an integer of 3-7;
Pro-(SerPO$_4$-Leu)$_n$-SerPO$_4$-Pro wherein n is an integer of 3-7;
Pro-(TyrPO$_4$-Leu)$_n$-TyrPO$_4$-Pro wherein n is an integer of 3-7;
Pro-(Glu-Phe-Ser-Phe)$_n$-Glu-Pro wherein n is an integer of 3-7;
Pro-(SerPO$_4$-Phe-Ser-Phe)$_n$-Ser-Pro wherein n is an integer of 1-4;
Pro-(SerPO$_4$-Phe-Glu-Phe)$_n$-Glu-Pro wherein n is an integer of 1-4;
Pro-(SerPO$_4$-Phe-Asp-Phe)$_n$-Asp-Pro wherein n is an integer of 1-4; and
Pro-Glu-(Phe-Glu)$_n$-(Gly)$_m$-Arg-Gly-Asp wherein n is an integer of 2-15 and m is an integer of 0-10.

According to a specific embodiment the amphiphilic peptide of the invention comprises a sequence selected from the group consisting of:

| | |
|---|---|
| Pro-(Ser-Phe)$_5$-Ser-Pro; | (SEQ ID NO: 3) |
| Pro-(SerPO$_4$-Phe)$_5$-SerPO$_4$-Pro; | (SEQ ID NO: 4) |
| Pro-(TyrPO$_4$-Phe)$_5$-TyrPO$_4$-Pro; | (SEQ ID NO: 5) |
| Pro-(Glu-Leu)$_5$-Glu-Pro; | (SEQ ID NO: 6) |
| Pro-(Asp-Leu)$_5$-Asp-Pro; | (SEQ ID NO: 7) |
| Pro-(Ser-Leu)$_5$-Ser-Pro; | (SEQ ID NO: 8) |
| Pro-(SerPO$_4$-Leu)$_5$-SerPO$_4$-Pro; | (SEQ ID NO: 9) |
| Pro-(TyrPO$_4$-Leu)$_5$-TyrPO$_4$-Pro; | (SEQ ID NO: 10) |
| Pro-(Glu-Phe-Ser-Phe)$_4$-Glu-Pro; | (SEQ ID NO: 11) |
| Pro-(SerPO$_4$-Phe-Ser-Phe)$_4$-Ser-Pro; | (SEQ ID NO: 12) |
| Pro-(SerPO$_4$-Phe-Glu-Phe)$_4$-Glu-Pro; | (SEQ ID NO: 13) |
| Pro-(SerPO$_4$-Phe-Asp-Phe)$_4$-Asp-Pro; | (SEQ ID NO: 14) |
| Ala-Leu-Glu-(Phe-Glu)$_3$-Pro-Ala-(Glu-Phe)$_3$-Glu-Leu-Pro-Ala-Leu-Glu-(Phe-Glu)$_3$-Pro; | (SEQ ID NO: 15) |
| Pro-Glu-(Phe-Glu)$_2$-Lys-(Glu-Phe)$_2$-Glu-Pro; | (SEQ ID NO: 16) |

-continued

Pro-Glu-(Phe-Glu)₅-(Gly)₃-Arg-Gly-  (SEQ ID NO: 17)
Asp-Ser;

(Phe-Glu)₃-Pro-(Gly)₃-Arg-Gly-Asp-  (SEQ ID NO: 18)
Ser;

Ac-Pro-Asp-(Phe-Asp)₅-Pro-NH₂;;  (SEQ ID NO: 19)

Pro-Asp-(Phe-Asp)₆;  (SEQ ID NO: 20)
and (Phe-Asp)₆.  (SEQ ID NO: 21)

In another embodiment the peptide can be a peptide analog, chemical derivative, or a pharmaceutically acceptable salt thereof. According to specific embodiments the derivatives include phosphorylated, amidated and acetylated peptides. Additionally, the peptide sequences can be chemically bound to a hydrophobic moiety, i.e. a lipid tail, a repeat of hydrophobic amino acids, or to any molecule which increase the permeability of the peptide. One lysine residue per each about 9 amino acids or more can be incorporated along the peptide to increase solubility in aqueous solution and to improve synthesis and purification yields. In one embodiment the peptide comprises the sequence Pro-Glu-(Phe-Glu)₂-Lys-(Glu-Phe)₂-Glu-Pro where Lys may induce a reverse turn. According to some embodiments the peptides are provided as multimers comprising linked repeats of the same sequence or of different sequences. According to other embodiments, mixtures of peptides according to the invention are provided. Preferably peptide mixtures and peptide multimers comprise peptides of similar lengths, yet peptide of different length may also be mixed or linked together. Without being bound to theory, the inclusion of peptide of a different length may affect the rheological properties of the hydrogel.

In another embodiment, a bioactive sequence is incorporated into the peptides of the invention. One non-limiting sequence is the trimer RGD (Arg-Gly-Asp), which is known to play a role in cell adhesion. An exemplary peptide including RGD is: Pro-Glu-(Phe-Glu)ₙ-(Gly)ₘ-Arg-Gly-Asp, wherein n is an integer of 2-20 and m is an integer of 0-10.

In another aspect the present invention provides a pharmaceutical composition comprising at least one amphiphilic peptide comprising at least 2 pair of alternating hydrophobic/hydrophilic amino acid residues, or a derivative or a salt thereof, capable of forming a β-sheet structure and promoting biomineralization, wherein the peptide comprises:
  i. 2-20 pairs of hydrophobic-hydrophilic alternating amino acid residues wherein the hydrophilic amino acid side chain is selected from the group consisting of: a negatively charged amino acid, a hydroxyl-containing amino acid, and a phosphorylated-hydroxyl-containing amino acid; and
  ii. no more than 10% positively charged amino acid residues;
an aqueous medium in which the peptide is dissolved, and a pharmaceutically acceptable carrier or excipient.

According to some embodiments the at least one amphiphilic peptide is 4-40 amino acids in length. According to some embodiments the at least one amphiphilic peptide is 7-28 amino acids in length. According to one embodiment the peptide comprises at least one terminal Pro residue. According to another embodiment the peptide comprises two terminal Pro residues. According to one embodiment the hydrophobic amino acid is selected from the group consisting of Phe, Leu, Ile, Val and Ala. According to another embodiment the hydrophobic amino acid is Phe or Leu. According to yet another embodiment the hydrophilic amino acid is selected from the group consisting of: Glu, Asp, Tyr, Ser, Thr, Ser(PO₄), Thr(PO₄), and Tyr(PO₄).

According to one embodiment the pharmaceutical composition comprises a peptide comprising an amino acid sequence according to Formula I:

$$X\text{-(hydrophobic-hydrophilic)}_n\text{-B} \quad \text{(Formula I)}$$

wherein n designates an integer of 2-20, hydrophobic designates a hydrophobic amino acid residue, hydrophilic designates a hydrophilic amino acid residue, X designates Pro, Pro-hydrophilic or represents the peptide's amino terminus, and B is Pro or represents the peptide's carboxy terminus.

According to some embodiments the amino terminus is modified, e.g., it may be acetylated. According to some embodiments the carboxy terminus is modified, e.g., it may be amidated.

According to a specific embodiment, the pharmaceutical composition comprises a peptide comprising an amino acid sequence selected from the group consisting of:
  X-(Phe-Glu)ₙ-B
  X-(Phe-Asp)ₙ-B
  X-(Leu-Glu)ₙ-B
  X-(Leu-Asp)ₙ-B
wherein n designates an integer of 2-20, X designates Pro, Pro-hydrophilic or represents the peptide's amino terminus, hydrophilic designates a hydrophilic amino acid residue, and B is Pro or represents the peptide's carboxy terminus.

According to some embodiments the amino terminus is modified, e.g., it may be acetylated. According to some embodiments the carboxy terminus is modified, e.g., it may be amidated.

According to one embodiment the pharmaceutical composition according to the invention comprises an amphiphilic peptide comprising a sequence selected from the group consisting of:
  Pro-Glu-(Phe-Glu)ₙ wherein n is an integer of 3-7;
  Glu-(Phe-Glu)ₙ-Pro wherein n is an integer of 3-7;
  Pro-(Ser-Phe)ₙ-Ser-Pro wherein n is an integer of 3-7;
  Pro-(SerPO₄-Phe)ₙ-SerPO₄-Pro wherein n is an integer of 3-7;
  Pro-(TyrPO₄-Phe)ₙ-TyrPO₄-Pro wherein n is an integer of 3-7;
  Pro-(Glu-Leu)ₙ-Glu-Pro wherein n is an integer of 3-7;
  Pro-(Asp-Phe)ₙ-Asp-Pro wherein n is an integer of 3-7;
  Pro-(Asp-Leu)ₙ-Asp-Pro wherein n is an integer of 3-7;
  Pro-(Ser-Leu)₅-Ser-Pro wherein n is an integer of 3-7;
  Pro-(SerPO₄-Leu)ₙ-SerPO₄-Pro wherein n is an integer of 3-7;
  Pro-(TyrPO₄-Leu)ₙ-TyrPO₄-Pro wherein n is an integer of 3-7;
  Pro-(Glu-Phe-Ser-Phe)ₙ-Glu-Pro wherein n is an integer of 3-7;
  Pro-(SerPO₄-Phe-Ser-Phe)ₙ-Ser-Pro wherein n is an integer of 1-4;
  Pro-(SerPO₄-Phe-Glu-Phe)ₙ-Glu-Pro wherein n is an integer of 1-4;
  Pro-(SerPO₄-Phe-Asp-Phe)ₙ-Asp-Pro wherein n is an integer of 1-4; and
  Pro-Glu-(Phe-Glu)ₙ-(Gly)ₘ-Arg-Gly-Asp wherein n is an integer of 2-15 and m is an integer of 0-10.

According to a specific embodiment the pharmaceutical composition according to the invention comprises an amphiphilic peptide comprising a sequence selected from the group consisting of:

| | |
|---|---|
| Pro-Glu-(Phe-Glu)$_5$; | (SEQ ID NO: 1) |
| Glu-(Phe-Glu)$_5$-Pro; | (SEQ ID NO: 2) |
| Pro-(Ser-Phe)$_5$-Ser-Pro; | (SEQ ID NO: 3) |
| Pro-(SerPO$_4$-Phe)$_5$-SerPO$_4$-Pro; | (SEQ ID NO: 4) |
| Pro-(TyrPO$_4$-Phe)$_5$-TyrPO$_4$-Pro; | (SEQ ID NO: 5) |
| Pro-(Glu-Leu)$_5$-Glu-Pro; | (SEQ ID NO: 6) |
| Pro-(Asp-Leu)$_5$-Asp-Pro; | (SEQ ID NO: 7) |
| Pro-(Ser-Leu)$_5$-Ser-Pro; | (SEQ ID NO: 8) |
| Pro-(SerPO$_4$-Leu)$_5$-SerPO$_4$-Pro; | (SEQ ID NO: 9) |
| Pro-(TyrPO$_4$-Leu)$_5$-TyrPO$_4$-Pro; | (SEQ ID NO: 10) |
| Pro-(Glu-Phe-Ser-Phe)$_4$-Glu-Pro; | (SEQ ID NO: 11) |
| Pro-(SerPO$_4$-Phe-Ser-Phe)$_4$-Ser-Pro; | (SEQ ID NO: 12) |
| Pro-(SerPO$_4$-Phe-Glu-Phe)$_4$-Glu-Pro; | (SEQ ID NO: 13) |
| Pro-(SerPO$_4$-Phe-Asp-Phe)$_4$-Asp-Pro; | (SEQ ID NO: 14) |
| Ala-Leu-Glu-(Phe-Glu)$_3$-Pro-Ala-(Glu-Phe)$_3$-Glu-Leu-Pro-Ala-Leu-Glu-(Phe-Glu)$_3$-Pro; | (SEQ ID NO: 15) |
| Pro-Glu-(Phe-Glu)$_2$-Lys-(Glu-Phe)$_2$-Glu-Pro; | (SEQ ID NO: 16) |
| Pro-Glu-(Phe-Glu)$_5$-(Gly)$_3$-Arg-Gly-Asp-Ser; | (SEQ ID NO: 17) |
| (Phe-Glu)$_3$-Pro-(Gly)$_3$-Arg-Gly-Asp-Ser | (SEQ ID NO: 18) |
| Ac-Pro-Asp-(Phe-Asp)$_5$-Pro-NH$_2$;; | (SEQ ID NO: 19) |
| Pro-Asp-(Phe-Asp)$_6$; and | (SEQ ID NO: 20) |
| (Phe-Asp)$_6$. | (SEQ ID NO: 21) |

According to specific embodiments the pharmaceutical composition comprises at least two different peptide sequences, mixed or covalently linked. According to another embodiment the pharmaceutical composition comprises pre-loaded mineral-salt solution or aggregates. According to a specific embodiment the pharmaceutical composition comprises tricalcium phosphate or hydroxyapatite. According to yet another embodiment the pharmaceutical composition comprises pre-loaded polysaccharides. According to a specific embodiment the pharmaceutical composition comprises a polysaccharide is selected from the group consisting of: hyaluronic acid, alginate or a sulfated polysaccharide such as a glycosaminoglycan. According to a more specific embodiment the polysaccharide is selected from the group consisting of chondroitin 4-sulfate, chondroitin 6-sulfate, dermatan sulfate, keratan sulfate, heparin, heparan sulfate, sucrose octasulfate, perlecan, syndecan, glypican and combinations thereof. According to a specific embodiment the pharmaceutical composition comprises alginate or hyaluronic acid. According to another specific embodiment the hydrogel comprises the peptide Ac-Pro-Asp-(Phe-Asp)$_5$-Pro-NH$_2$ and the polysaccharide alginate. According to a specific embodiment the pharmaceutical composition comprises calcified mineral powder or particulates.

According to some embodiments a composition comprising a mixture of one or more peptides is provided. In various embodiments the pharmaceutical composition further comprises at least one therapeutic agent. A therapeutic agent includes inter alia growth factors, cytokines, chemotherapeutic drugs, enzymes, anti-microbials, anti-resorptive agents and anti-inflammatory agents.

According to yet another embodiment the pharmaceutical composition of the present invention serve as a carrier for modified release of at least one therapeutic agent, e.g. slow release, sustained release etc.

The composition can be dispensed in many different forms, depending on the indication and discretion of the medical practitioner. In some embodiments the composition is a dry composition, for example particles, granules or powder, optionally obtained by lyophilization. In certain indications a fluid, or semi-fluid composition is provided. In preferred embodiments the pharmaceutical composition is a gel or a hydrogel. In some embodiments the pharmaceutical composition is useful as a coating for an implant.

According to yet another embodiment, peptides, proteins and other substances having osteogenic activity are linked to or mixed with amphiphilic peptides of the present invention. An exemplary osteogenic peptide is described in U.S. Pat. No. 7,163,920. Other active substances known to enhance bone and cartilage repair are angiotensinogen, angiotensin AI and its fragments and analogs, angiotensin AII and its fragments and analogs, bone morphogenic protein-2, bone morphogenic protein-4, bone morphogenic protein-6, bone morphogenic protein-7, transforming growth factor-beta, insulin-like growth factor, and parathyroid hormone.

In the reconstruction or repair of various injuries, in a structural tissue like bone, a solid composition may be desired. Accordingly, one aspect the present invention provides an implant comprising a hydrogel or at least one amphiphilic peptide according to the invention. In some embodiments the implant further comprises minerals such as calcium and phosphate. According to a specific embodiment the implant comprises tricalcium phosphate. The minerals are preferably provided as pre-loaded mineral salt solution or aggregates. The mineral salt concentration according to one embodiment is about 1-70% w/v. In some embodiments the implant comprises at least one peptide according to the present invention or a hydrogel according to the invention and at least one polysaccharide. According to specific embodiments the polysaccharide is a glycosaminoglycans. According to another specific embodiment the polysaccharide is alginate or hyaluronic acid. In various embodiments the implant comprises at least one peptide of the present invention and a metal structure. The implant can take on any shape including a sphere, screw, cube, rod, tube or plate.

The pharmaceutical composition of the present invention is useful for treating orthopedic, periodontal and craniofacial indications wherein there is need to fill a void in a bone, to secure a prosthetic device or a need to delivery therapeutic agents to the bone or tissue in contact with the bone. Tissue closely associated with bone includes, ligaments, tendons cartilage and muscle. The present invention fulfills the need for pharmaceutical compositions to enhance bone repair in a mammal suffering from bone fractures, defects, and disorders which result in weakened bones such as osteoporosis, osteoarthritis, Paget's disease, osteohalisteresis, osteomalacia, periodontal disease, bone loss resulting from multiple myeloma and other forms of cancer, bone loss resulting from side effects of other medical treatment (such as steroids), and age-related loss of bone mass. In addition, bony ingrowth into various prosthetic devices can be greatly enhanced so that such artificial parts are firmly and permanently anchored into the surrounding skeletal tissue through a natural osseous bridge.

In accordance with the invention, at least one amphiphilic peptide of 4-40 amino acids comprising at least 2 dyads of alternating hydrophobic/hydrophilic amino acid residues, or an analog, derivative or a salt thereof, capable of forming a β-sheet structure and inducing biomineralization, and a pharmaceutically acceptable carrier, are used for the preparation of a therapeutic medicament for treatment of a bone disorder. The medicament is useful for treating diseased or injured bone in orthopedic, periodontal and craniofacial indications wherein the medicament is provided alone or comprising therapeutic agents that may, inter alia, accelerate the healing rate and enhance the quality of bone formation or treat a disease or traumatized bone associated tissue.

The pharmaceutical composition according to the present invention can be supplied as a ready-to-use product or as a basic composition to which a surgeon is capable of adding any mineral, therapeutic agent or polymer according to the instant requirements of the patient in need thereof.

The invention further relates to a method for the prevention and/or treatment of a bone disorder said method comprising administering to a subject in need thereof a therapeutically effective amount of a pharmaceutical composition of the invention. The bone disorder include but is not limited to: bone fractures, defects, and disorders which result in weakened bones such as osteoporosis, osteoarthritis, Paget's disease, osteohalisteresis, osteomalacia, periodontal disease, bone loss resulting from multiple myeloma and other forms of cancer, bone loss resulting from side effects of other medical treatment (such as steroids), and age-related loss of bone mass.

Depending on the indication the peptides and matrices thereof may be used per se or as part of an implant. According to one embodiment the composition is a powder and is used per se. According to another embodiment a gel-like material is administered directly to a bone defect. According to a specific embodiment the gel-like material is inserted into a syringe for local administration. The peptides of the invention serve as a template for the in situ formation and development of bone.

According to another aspect the present invention provides a method for preparing a hydrogel composition. The method comprises the following steps:

a) providing a liquid solution comprising at least one amphiphilic peptide of 4-40 amino acids comprising at least 2 pair of alternating hydrophobic/hydrophilic amino acid residues, or an analog, derivative or a salt thereof, capable of forming a β-sheet structure and inducing biomineralization in a vessel;

b) providing a solution comprising ionic calcium, optionally further comprising a therapeutic agent;

c) mixing together the peptide composition and the solution;

d) allowing the mixture to precipitate or to form a hydrogel;

e) separating a peptide/precipitate solid composition from the solution.

According to one embodiment the ionic calcium of (b) is selected from the group consisting of: calcium chloride salt, phosphate salt, particles or particulates of calcium phosphate mineral, tricalcium phosphate and hydroxyapatite. According to some embodiments the liquid solution comprises ion concentrations similar to those in the human blood plasma (simulated body fluid-SBF). In some embodiments the solution of step b) further comprises at least one therapeutic agent.

Another method for preparing hydrogel comprises: a) providing the peptide in solid/powder form which may optionally comprise powder or particles of a calcium phosphate mineral; b) providing an alkaline (high pH) solution; and c) mixing the solid peptide composition with the alkaline solution.

In various embodiments the peptide composition of the present invention serves as a coating on orthopedic implants; for example Titanium (Ti) or Ti alloy samples.

Furthermore, the composition may be used as a coating on synthetic or other implants such as pins and plates, for example, in hip replacement procedures. Thus, the present invention further provides implants or medical devices coated with the peptides or peptide matrix of the invention.

In yet another aspect, the present invention provides a kit comprising the peptides of the present invention and optionally further comprising a pharmaceutically acceptable carrier or excipient and an optional means for delivery of the composition. In some embodiments the dry and liquid components may be present in separate containers in the kit, or some of the components may be combined within one container.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 1A-1B show a schematic illustration of the seven-residue peptide PE(FE)$_2$P (upper white stick figure) on hydroxyapatite (gray stick figures). The calcium ions in HA lattice (balls) are positioned at distances that match characteristic distances in β-sheet. The 9.432 Å axis is twice the distance of ~4.7 Å, thus there is a match between calcium ions along the a/b axes and hydrophilic amino acids in every second β-strand (FIG. 1B). The 6.881 Å along the c axis equals the distance between hydrophilic amino acids along a β-strand (FIG. 1A).

FIG. 6 Representative forms of calcium-phosphate particles on $P_{FD}$-13 that was incubated over $SBF_{1.5}$ solution as observed by TEM top and SEM bottom images. These features may be observed already after 5 days, the scale bar for all images is 0.2 µm unless otherwise indicated. After 21 days of incubation the peptide monolayer adsorbs minerals to the point that it becomes visible to naked eye.

FIG. 8 shows optical microscope images of SaOS-2 cells cultures over $P_{FE}$-13 (right) $P_{FD}$-13 (center) and over cover slip.

DETAILED DESCRIPTION OF THE INVENTION

Advanced approaches in tissue engineering utilize polymer scaffolds to generate a supporting and controlled environment for tissue formation. According to the present invention a novel multifunctional peptide template matrix (PTM) was designed, prepared and tested for bone tissue engineering. It is shown for the first time that the PTM acts as a scaffold for the bone mineral hydroxyapatite (HA) formation and for bone cell adhesion and proliferation. The present invention is based on an interdisciplinary approach that combines peptide design, control over mechanism of HA biomineralization and tissue engineering aspects. The PTMs according to the present invention are de-novo designed peptides, rich in acidic amino acids, amenable of assembling into beta-sheet fibers and forming hydrogels. These peptides are also capable of attracting positively charged calcium ions which are essential to bone formation. The beta-sheet structure that is characterized by dimensions that are very similar to those of HA induces the crystallization of calcium and phosphate ions en-route to HA phase.

The present invention is directed to compositions comprising synthetic peptides for in vitro and in situ biomineralization having utility in orthopedic and periodontal applications.

In principle, an exemplary bone repair or regenerating material will exhibit the following properties:
i. Biocompatibility: minimal toxicity to the patient and maximal similarity to natural bone;
ii. Osteoconductivity: provide a milieu amenable to recruitment, attachment, migration and proliferation of cells involved in bone growth; and
iii. Convenience: easy to use by the medical practitioner.
In addition, the bone enhancing material may also exhibit the following properties:
iv. Osteoinductivity: capacity to induce regeneration or enhancement of functional bone; and
v. Biodegradability: capacity to degrade and be replaced by natural bone.

Figure 2:
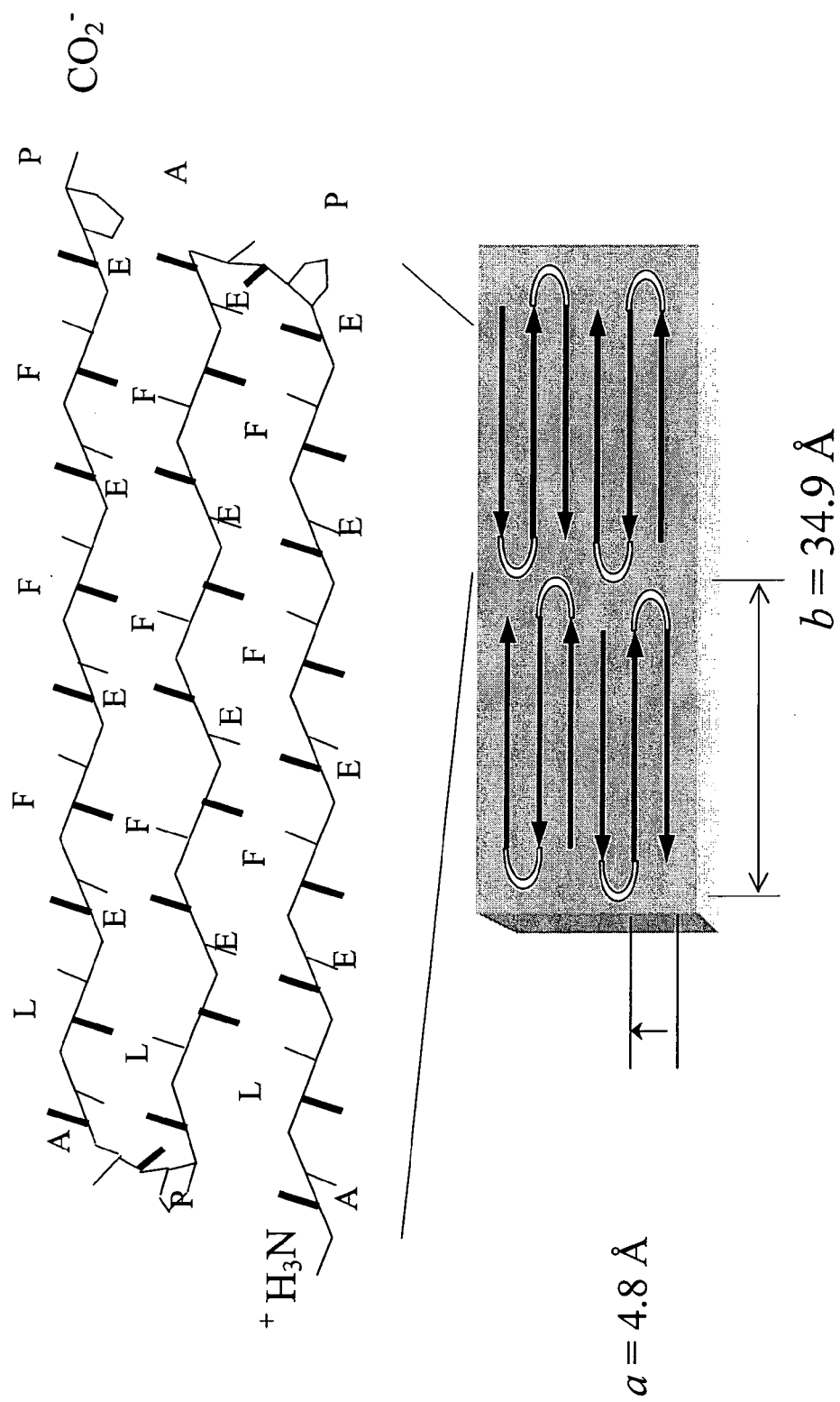
FIG. 2 shows a schematic representation of a triple stranded peptide (top) that incorporates two β-hairpin motifs, showing peptide backbone (line), carbonyl and amine groups (thick and thin lines, respectively). Amino acid side chains are assigned the known one letter code (P=proline, E=glutamic acid, F=phenylalanine, A=alanine, L=leucine). A theoretical model for the assembly of peptides at a hydrophilic/hydrophobic interface is shown in the bottom of FIG. 2.

The present invention provides a composition comprising peptides exhibiting the aforementioned advantageous properties. Without wishing to be bound to theory, the amphiphilic peptides disclosed herein have three primary characteristics that make them unexpectedly advantageous for biomineralization and associated bone repair and tissue engineering applications:
i. The peptides comprise alternating hydrophilic and hydrophobic amino acids that provide the peptide with the propensity to assume a β-sheet structure, which exhibits repeating molecular distances similar to the dimensions of a HA unit cell (FIG. 1). The β-sheet structure may also be formed by peptides that fold into β-hairpin structure that is induced by Pro-Ala at positions i and i+1 (FIG. 2);
ii. The hydrophilic amino acids are either negatively charged (Glu, Asp) or hydroxylated (Ser, Thr, Tyr), or hydroxylated and chemically modified by a phosphate group (Ser-$PO_4$, Thr-$PO_4$, Tyr-$PO_4$). By specific patterning of these amino acids along the peptide backbone it is possible to perfect the apparent pKa of the peptide, the $Ca^{+2}$ attraction to the peptide template, and also to position the $Ca^{+2}$ binding amino acids (i.e. all the above mentioned amino acids, excluding the hydroxylated amino acids), at specific sites on the peptide that match specific crystalline planes of the HA lattice;
iii. The amino acid Pro may be positioned at either or both peptide termini to induce the two-dimensional ordering in monolayers or to affect the extent of junction formation in hydrogels, of the amphiphilic molecules.

The amphiphilic peptides of the present invention may form two-dimensional (2D) coatings over surfaces (glass, metals, metal oxides minerals etc.) by for example, adsorption from solution or by deposition in the Langmuir-Blodgett methods (Birdi 1999). These peptides also form self-supporting three-dimensional matrices in solution by adjusting pH or ionic strength.

The peptide matrices may further be mixed with HA, tricalcium phosphate (TCP) or other calcium-phosphate (Ca/P) powder or particles and/or polysaccharides and/or with biocompatible polymers such as PGA/PLGA and/or phospholipids. Additionally, the peptide sequences can be chemically bound to a hydrophobic moiety, i.e. a lipid tail, or a repeat of hydrophobic amino acids. Without wishing to be bound to theory, a hydrophobic moiety may control the solubility of the peptide, make it less soluble in aqueous solution. It may also tune the peptide tendency to form fibrils and to hydrogel.

DEFINITIONS

For convenience and clarity certain terms employed in the specification, examples and claims are described herein.

The term "biomineralization" refers to the deposition of inorganic solids in biological systems.

The term "peptide" as used herein is meant to encompass natural, non-natural and/or chemically modified amino acid residues, each residue being characterized by having an amino and a carboxy terminus, connected one to the other by peptide or non-peptide bonds. The amino acid residues are represented throughout the specification and claims by either one or three-letter codes, as is commonly known in the art. The peptides of the present invention are preferably utilized in a linear form, although it will be appreciated that in cases where cyclization does not severely interfere with peptide characteristics, cyclic forms of the peptide can also be utilized.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, either the L or D isomers may be used.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Also included within the scope of the invention are salts of the peptides, fragments, analogs, and chemical derivatives of the peptides of the invention.

As used herein the term "salts" refers to both salts of carboxyl groups and to acid addition salts of amino groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

A "chemical derivative" as used herein refers to peptides containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Preferred chemical derivatives include peptides that have been phosphorylated, C-termini amidated or N-termini acetylated.

"Functional derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

Peptide analogs include amino acid substitutions and/or additions with natural or non-natural amino acid residues, and chemical modifications which do not occur in nature. Peptide analogs include peptide mimetics. A peptide mimetic or "peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "analogs" may be computer assisted. Additional peptide analogs according to the present invention comprise a specific peptide or peptide analog sequence in a reversed order, namely, the amino acids are coupled in the peptide sequence in a reverse order to the amino acids order which appears in the native protein or in a specific peptide or analog identified as active. Whether completely or partially non-peptide, peptidomimetics according to this invention provide a spatial arrangement of chemical moieties that closely resembles the three-dimensional arrangement of groups in the peptide on which the peptidomimetic is based. As a result of this similar active-site structure, the peptidomimetic has effects on biological systems, which are similar to the biological activity of the peptide.

The salts, analogs and the chemical derivatives of the peptides are preferably used to modify the pharmaceutical properties of the peptides insofar as stability, solubility, etc. are concerned.

A "peptide template matrix (PTM)" is used to describe a network of hydrogen bonded peptides, in monolayers, hydrogels, membranes or an intermediate form. The term "peptide template matrix" also refers to molecular templates that provide 2-dimensional ordered structures, that exhibit acidic functionalities at spacing compatible with biomineralization, for example with $Ca^{+2}$ positions in the planes of the HA mineral. These molecular templates may assemble into fibers that generate three-dimensional gel or non-ordered assemblies, both to which we refer as matrices.

The term "hydrogel" according to the present invention refers to a three-dimensional well hydrated polymeric porous matrix of bioactive nanofibers comprising amphiphilic peptides in β-sheet conformation. This definition includes dry "hydrogel forming peptides" that will swell in aqueous environments, as well as water-swollen materials. A hydrogel according to the present invention can be tailored to possess a range of properties depending on the peptides of which the hydrogel is composed and on additional materials which may be added such as, mineral solutions or aggregates, polysaccharides, active ingredients, exepients and more.

The term "amphiphile" refers to a molecule, in this case a synthetic peptide, possessing both hydrophilic and hydrophobic nature. A compound with such properties is called "amphiphilic".

The term "biocompatible" as used herein refers to materials having affinity with living tissues, low toxicity and no unacceptable foreign body reactions in the living body. For example, the peptides and peptide matrices of the present invention are biocompatible The term "osteoconductive" as used herein refers to materials that provide a microenvironment that is advantageous to the healing of diseased or damaged bone. Preferably, the composite of the invention provides a milieu that is advantageous to the infiltration and proliferation of cells involved in the process of bone repair.

This term "implantation" refers to the insertion of the composition of the invention into a subject, whereby the peptide or matrix comprising a peptide of the invention or an implant comprising the peptide of the invention serves to replace, fully or partially, tissue that has been damaged or removed. Another aspect of implantation is also taken to mean the use of the composition as a vehicle to transport therapeutic agents to a certain site in a patient. In this aspect there is also included the incorporation into the composition or implant of a therapeutic agent selected from growth factors, cytokines, chemotherapeutic drugs, enzymes, anti-microbials, anti-inflammatory agents. A subject is preferably a mammalian subject, and more preferably a human subject.

The term "injection" refers to the insertion of a composition of the invention into a mammal using a syringe or other device, which allows administration of the peptide composition directly to the site of treatment. Another aspect of injection is also taken to mean the use of the composition as a vehicle to transport therapeutic drugs and therapeutic agents to a certain site in a patient. In this aspect there is also included the introduction into the composite of a therapeutic agent selected from growth factors, cytokines, enzymes, anti-microbials, anti-inflammatory agents and chemotherapeutic agents such as anti-cancer drugs.

Therapeutic agents including growth factors, angiogenic factors, and the like, are advantageous to encourage a more rapid growth of the cells within the composite, or a more rapid vascularization of the material thus reducing the healing time.

The term "physiologically acceptable carrier" or "diluent" or "excipient" refers to an aqueous or non-aqueous fluid that is well suited for pharmaceutical preparations. Furthermore, the term "a pharmaceutically acceptable carrier or excipient" refers to at least one carrier or excipient and includes mixtures of carriers and or excipients. The term "therapeutic" refers to any pharmaceutical, drug or prophylactic agent which may be used in the treatment (including the prevention, diagnosis, alleviation, or cure) of a malady, affliction, disease or injury in a patient.

Biomineralization

Biomineralization has been defined as the highly regulated process that produces materials such as bones, shells and teeth that have specific biological functions and structures. These and similar biologically controlled materials are characterized by specific crystallographic and chemical properties, which include: rather uniform particle size, well-defined structures and compositions, high level of spatial organization, preferred crystallographic orientation and higher order assembly into hierarchical structures (Mann, 2001).

The term "nucleus" as used herein, refers to clusters of ions of nanoscale dimensions, which resemble a small piece of the bulk crystalline phase. There is little structural information about the initial states formed in mineral precipitation. The nucleus comprises strongly interacting ions so that the particulate energy overcomes solvation and surface energy. Although ions in the nuclei are relaxed to some degree from their normal unit cell positions there is still close correspondence between the lattice parameter of the nucleus structure and the bulk mineral phase.

Biomineralization may take place within four main biological sites: on the cell (epicellular), in the space between closely packed cells (intercellular), inside the cell (intracellular) and within insoluble macromolecular framework outside the cell (extracellular). In general, two types of assembled organic structures are used to delineate the mineralization sites: lipid vesicles within the cell and macromolecular frameworks outside the cell. Intercellular biomineralization usually takes place within vesicles that form controlled microenvironment for nucleation. However, large bone structures are constructed in the extracellular region, where biomineralization is regulated through the activity of specialized cells that seal off a space into which an organic matrix, consisting of insoluble proteins and polysaccharides, is secreted. This complex of macromolecules, or organic matrix, serves as a template that controls the nucleation process through an inorganic-organic interface (Boskey, 1998; Weiner, 1997; Mann, 1988). In general, this organic matrix can be divided into two classes of macromolecules: a) framework, insoluble fraction of the bone organic matrix, which is primarily collagen; and b) acidic polypeptides and polysaccharides, proteoglycans, glycoproteins, which control the structural and functional characteristics of the matrix.

Homogeneous and Heterogeneous Nucleation

The term "homogeneous nucleation" refers to spontaneous formation of nuclei in a supersaturated solution The term "heterogeneous nucleation" refers to the formation of nuclei on the surface of a substrate present in crystallization medium. Homogeneous nucleation occurs due to thermodynamically driven, spontaneous formation of nuclei in supersaturated solutions. Heterogeneous nucleation is initiated with the formation of nuclei on a substrate surface that is present in an aqueous medium. Heterogeneous nucleation occurs at lower saturation levels than those required for homogeneous nucleation since the presence of an external substrate can significantly reduce the interfacial energy created along with the nuclei formation. In heterogeneous nucleation, nuclei are stabilized by attachment to a foreign surface particularly if there is chemical and structural complimentary.

Biomineralization is controlled by chemical, spatial and structural mechanism, for example:

a) Chemical control is related to the type of functional groups (carboxyls, phosphate) that tend to bind to the growing crystal or nuclei. It is also related to the solubility product (Ksp) that is crucial for determining the thermodynamic limit for precipitation of ionic materials. Precipitation occurs when ion concentrations in solution are greater than their Ksp equilibrium value. The difference between ion concentrations in solution and in equilibrium determines the degree of saturation of the solution. An increase in supersaturation rapidly increases the thermodynamic driving force for precipitation since it decreases the activation energy for nucleation.

b) Spatial control is the regulation of size and shape of biominerals by restricting the deposition to define spaces such as organic frameworks.

c) Structural control, or epitaxis, enables nucleation of a certain face on an insoluble crystalline substrate, the organic matrix interface, and is associated with the concept of lattice matching.

Two properties of organic matrices are thought to be essential for specific nucleation:
d) attraction of inorganic ions to binding sites at the organic matrix; and ii) specific arrangement of the matrix to control orientation, size and morphology of the growing crystal (Mann, 1988).

Biomineralization of Bone

Hydroxyapatite (HA) having chemical formula $Ca_{10}(PO_4)_6(OH)_2$, is one of the major constituents of the inorganic components in bone as well as in other human hard tissues (Posner, 1969; Mann, 2001) The mineralization of bone occurs by deposition of HA in an organic extracellular matrix composed of collagen and other proteins, many of which are rich in acidic residues (Hunter, 1996; Teraub, 1989). Collagen provides the general framework for the deposition of proteins and HA, so that the composite HA-matrix exhibits the necessary structural orientation (Mann, 1988). The non-collagenous acidic-rich proteins are thought to be involved in nucleation and in modulating HA formation (Boskey, 1998; Oliveira, 2003). In addition to regulating nucleation, the organic-inorganic composite structure provides the mechanical and structural properties necessary for functional bone tissue.

HA enables formation of bone on its surface by supporting attachment, migration, proliferation, and differentiation of bone forming cells, osteoblasts (Oliveira, 2003; Delange, 1989). The mechanical properties of the HA alone, in absence of organic matrix onto which it deposits in vivo, does not resemble natural human bone. In fact, HA is stiff and often very brittle and thus cannot be used as is, for load-bearing applications.

Biomineralization at Organic Interfaces

The two main properties of organic interfaces that lead to specificity in nucleation of biominerals are electrostatic accumulation and structural correspondence.

Electrostatic accumulation is considered to be the initial step in biomineralization. It is believed that the bone acid-rich proteins and possibly also collagen control nucleation via charged amino acids on their surfaces. Without wishing to be bound to theory, the acidic and phosphorylated amino acids, which at biological pH, expose charged functional groups, i.e. negatively charged carboxylate groups of glutamic acid and aspartic acid as well as negatively charged phosphates. (Addadi, 1985; Mann, 1988) are involved in binding $Ca^{+2}$ ions and in initiating the mineralization process.

β-Sheet Self Assembly at Interfaces

DeGrado and Lear (DeGrado, 1985) showed that amphiphilic peptides comprising repetitive dyads of hydrophilic and hydrophobic amino acid residues tend to self assemble into β-pleated sheet structure at air-water interfaces. The assembly of β-sheet peptides into one-dimensional (1D) ribbons is mediated by inter-strand hydrogen bonds along the direction that is normal to the peptide strand. The flexibility of the peptide backbone and the repetitive nature of the hydrophilic-hydrophobic amino acid motif may induce dislocation defects that inhibit the 2D ordered structure. The present inventor and others (Rapaport, 2000) obtained 2D order β-strand assemblies at air-water interfaces by using peptides terminated with proline (Pro) residues. Pro was chosen to be the terminal amino acid since it is a potent disrupter of β-sheet structure. Without wishing to be bound to theory, Pro termini minimize free motion and dynamic disorder at the ribbon edges due to geometric constrains imposed by the cyclic side chains. The electrostatic interactions between the chain termini contribute to juxtaposition of the β-sheet ribbons.

Accordingly, the present invention has shown that peptide sequences comprising alternating hydrophilic-hydrophobic amino acid repeats where the hydrophilic amino acids are negatively charged can form hydrogels and other matrices and that these matrices are useful in the formation of calcium phosphate mineralization and thus useful for bone regeneration, for both in situ and in vitro uses.

Without wishing to be bound to theory, a repetitive β-sheet structure i.e. 4.7 Å and 6.9 Å, are in excellent correlation with HA crystal unit cell dimensions, a=b=9.432 Å and c=6.881 Å. Accordingly it is evident that calcium ions in HA lattice are positioned at distances that match characteristic distances in β-sheet. The 9.432 Å axis is twice the distance of ~4.7 Å, thus there is a match between calcium ions along a/b axes and hydrophilic amino acids in every second β-strand (FIG. 1B). The 6.881 Å along the c axis equals the distance between hydrophilic amino acids along a (β-strand (FIG. 1A).

The crystal growth of calcium phosphate species in solution may occur via sequential modifications of intermediate amorphous or ordered phases. It is possible that amorphous phases will first precipitate followed by the formation of minerals with decreasing solubility.

Other than HA, several other Ca/P phases have been identified as intermediates in the biomineralization of Ca/P (Mann, 2001). Furthermore, it was found that Ca/P phases in aqueous solutions mainly include octacalcium phosphate (OCP) and dicalcium phosphate dehydrate (DCPD) (Iijima, 1998). Since hydroxyapatite is considered the most thermodynamically stable in physiological environment, and OCP and DCPD are kinetically favorable, they are regarded as metastable phases of Ca/P (Iijima, 1998; Suvorova, 2001) that transform over time to the thermodynamically stable form of hydroxyapatite.

Matrix Preparation

The peptides, fragments, derivatives and analogs thereof, are preferably synthesized using conventional synthesis techniques, e.g., by chemical synthesis techniques. These methods include exclusive solid phase synthesis, partial solid phase synthesis methods, fragment condensation, classical solution synthesis. Solid phase peptide synthesis procedures are well known in the art and further described by John Morrow Stewart and Janis Dillaha Young, Solid Phase Peptide Syntheses (2nd Ed., Pierce Chemical Company, 1984). A skilled artesian may synthesize any of the peptides of the present invention by using an automated peptide synthesizer using standard chemistry such as, for example, t-Boc or Fmoc chemistry. Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Alternatively, the peptides and other constructs of the present invention may be prepared by known recombinant DNA techniques by cloning and expressing within a host microorganism or cell a DNA fragment carrying a coding sequence of the selected peptide or construct. Such techniques were described for example, by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463. Coding sequences for the peptides can be prepared synthetically, or can be derived from viral RNA by known techniques, or from available cDNA-containing plasmids. According to some embodiments the present invention provides a pharmaceutical composition comprising a peptide having a sequence selected from SEQ ID NO:1-SEQ ID NO:21 or peptide matrix thereof and a pharmaceutically acceptable carrier or excipient. According to one embodiment of the present invention the pharmaceutical composition further comprises at least one therapeutic agent. A suitable therapeutic agent can be selected from the group consisting of antibiotics, antiviral agents, chemotherapeutic agents, anti-rejection agents, analgesics and analgesic combinations, anti-inflammatory agents, hormones, growth factors and cytokines. Any additives to the composition may be added at any time, including during preparation of the composition or before, during or after administration to eth subject.

Cellular tissue matrices may be prepared by removing cellular components form tissue via mechanical and chemical manipulation and mixing with the hydrogel to produce cellular matrices as described for example in Koh and Atala 2004, or by other methods known in the art.

The pharmaceutical composition of the present invention is useful for treating orthopedic, periodontal and craniofacial indications wherein there is need to fill a void in a bone including fractures, non-union fractures, spinal fusion and other indications. According to certain embodiments the pharmaceutical composition is useful for the delivery of therapeutic agents to a bone lesion or defect. According to other embodiments, the pharmaceutical composition of the present invention is useful for cementing prostheses or to prevent osteolysis.

In accordance with the invention, provided is the use of at last one peptide of the invention for the manufacture of a medicament for treating diseased or injured bone in orthopedic, periodontal and craniofacial indications wherein the peptides are provided alone or comprising therapeutic agents. A therapeutic agent can be selected for example, to accelerate the healing rate and enhance the quality of bone formation.

According to one embodiment of the present invention a biocompatible polymer or mixture thereof is incorporated in the pharmaceutical composition of the invention. Suitable polymers include natural and synthetic polymers. Examples of natural biocompatible polymers include polysaccharides and oligosaccharides. According to one embodiment of the present invention the natural biocompatible polymer is a polysaccharide, preferably hyaluronic acid, alginate or a sulfated polysaccharide such as a glycosaminoglycan selected from the group consisting of chondroitin 4-sulfate, chondroitin 6-sulfate, dermatan sulfate, keratan sulfate, heparin, heparan sulfate, sucrose octasulfate, perlecan, syndecan, glypican and combinations thereof. Heparin is meant to encompass the various derivatives of heparin including very low molecular weight heparin, low molecular weight heparin, heparan, and heparin mimetics. Hyaluronic acid is meant to encompass cross-linked and non-crosslinked hyaluronic acid derivatives. Additional natural biocompatible polymers include starch, collagen, gelatin, glycogen, chitin, cellulose, keratins or combinations thereof. The polysaccharide improves the hydrogel's chemical and rheological properties.

Synthetic polymers include non-biodegradable or biodegradable material. Examples of non-biodegradable materials include polytetrafluoroethylene, perfluorinated polymers such as fluorinated ethylene propylene, polypropylene, polyethylene, polyethylene terapthalate, silicone, silicone rubber, polysufone, polyurethane, non-degradable polycarboxylate, non-degradable polycarbonate, non-degradable polyester, polyacrylic, polyhydroxymethacrylate, polymethylmethacrylate, polyamide such as polyesteramide, and copolymers, block copolymers and blends of the above materials.

Examples of biodegradable materials include hydrolyzable polyesters such as polylactic acid and polyglycolic acid, polyorthoesters, degradable polycarboxylates, degradable polycarbonates, degradable polycaprolactones, polyanhydride, and copolymers, block copolymers and blends of the above materials.

The pharmaceutical composition of this invention may be administered as a gel, preferably as an injectable gel. Alternatively, an implant comprising the peptide of the invention is provided. Furthermore, the peptide or peptide matrix thereof may be used as cement for or as a coating on synthetic or other implants such as pins and plates, for example, in hip replacement procedures. Thus, the present invention further provides implants or medical devices coated with the peptides or matrices of the invention.

In certain applications, a solid implant is desired. According to one embodiment the present invention provides a bone substitute composition comprising a peptide of the present invention or a peptide matrix thereof and optionally further comprising a therapeutic agent. In some embodiments the therapeutic agent is an anti-resorptive agent, for example bis-phosphonate. An implant comprising a peptide according to the invention and at least one anti-resorptive agent has attributes that make it particularly advantageous for enhancing and preserving bone in vivo and for applications such as securing prosthetic devices to bone and filling lesions due to osteolytic processes such as metastases.

A solid composition, for example an implant, may be achieved by providing a peptide matrix and a solution of minerals. The method of preparing an implant for the treatment of a bone defect comprises the following steps:

a) providing a composition comprising a peptide the peptide comprising an amino acid sequence selected from SEQ ID NO:1-SEQ ID NO:21;

b) subjecting said peptide to conditions for self assembly into β-sheets;

c) providing a solution comprising ionic calcium, phosphate, optionally further comprising a therapeutic agent;

d) mixing together the peptide composition and the solution;

e) allowing the mixture to precipitate;

The composition of step a) comprises a peptide at about 0.10 mg/ml to about 100 mg/ml, preferably at about 10 mg/ml.

The conditions for calcium ion that may be, for example, calcium chloride added to a concentration of about $10^{-3}$ to about 1M.

The phosphate may be $NaH_2PO$, added to a concentration of about $10^{-3}$ to about 1M.

The composition may be sterilized for use in vivo, in particular for use in clinical and therapeutic applications in mammals The peptides or peptide matrices of the invention may be used in particle or powder form, or may be combined with a physiological liquid for use as a gel-like material. Alternatively a preformed implant comprising the peptide of the invention is provided. Furthermore, the composite may be used as a coating on synthetic or other implants such as pins and plates, for example, in hip replacement procedures. Thus, the present invention further provides implants or medical devices coated with the matrix of the invention.

Therapeutic Use

Fractures and other defects in long bones heal via a process known as endochondral ossification while defects and lesions in intramembranous bones heal via an osteogenic route. Four stages of fracture repair have been characterized (reviewed in Bolander, 1992). Stage 1 is the immediate injury response; stage 2 marks the synthesis of new bone matrix and callus formation in a process termed intramembranous ossification; stage 3, designated chondrogenesis, occurs as the mesenchymal cells develop into chondrocytes and are eventually replaced by cartilage; stage 4 is the formation of bone from cartilage in a process known as endochondral ossification.

According to the principles of the present invention the peptides of the invention are useful in indications where bone enhancement, bone substitution and bone healing is desired. According to one embodiment the peptides of the invention are suitable for use in orthopedic indications including periodontal surgery, and plastic and craniofacial surgery.

In a non-limiting example, the peptides of the present invention are useful for augmentation of the alveolar ridge to facilitate retention of denture and to fill various periodontal lesions. It is also useful to fill the gap in cases of bony defects, cysts and traumatic bone loss. The composite of the present invention is useful for maxillofacial dysplasia, filling of bone defects in skull, zygomatic and mandibular areas and augmentation of various bony areas. In addition, the composite of the present invention is useful to reconstruct the calvaria including repair of cranial base and temporal bone defects following surgery. Orthopedic applications in which the compositions of the invention are useful include, but are not limited to, fractures and non-union fractures resulting from a trauma or generated by surgical means, spinal fusion, hip resurfacing or bone augmentation in indications such as osteopenia or osteoporosis.

According to the principles of the present invention the peptide matrices or implants of the present invention comprise therapeutic agents that have the capacity to act at some or all of the stages in order to enhance bone repair, reduce inflammation or infection and ensure the formation of functional bone.

Kits

The present invention further provides a kit comprising the peptides, peptide matrices or implants of the present invention, where the dry and liquid components may be present in separate vessels in the kit, or some of the components may be combined into one vessel.

The following examples are intended to be merely illustrative in nature and to be construed in a non-limitative fashion.

EXAMPLES

The following examples demonstrate development of methodology for hydrogel formation by peptides rich in acidic amino acids at physiological pH's, characterization of hydrogels by rheometric measurements, induction of HA nucleation during formation of HA-composite-hydrogels, in model system composed of the acidic b-sheet peptide monolayers, formation of hydrogels amenable to 2-D and 3-D cell culture which support cell adhesion and proliferation.

Although the present invention has been described with respect to various specific embodiments thereof in order to illustrate it, such specifically disclosed embodiments should not be considered limiting. Many other specific embodiments will occur to those skilled in the art based upon applicants' disclosure herein, and applicants propose to be bound only by the spirit and scope of their invention as defined in the appended claims.

Example 1

Peptide Synthesis

The peptides were synthesized by conventional solid phase synthesis methods, using either tBOC or FMOC chemistry. The peptides of the invention may further be prepared using recombinant DNA techniques known in the art.

Example 2

Preparation of Peptide Hydrogel

In general the matrix can be formed in the following way: dissolving the peptides at high pH above about 8) using either buffer (Tris) or NaOH. With the addition of the peptide the pH of the mixture drops and hydrogel may form. The peptide that is dissolved in alkaline solution can be titrated with HCl to a pH ~7 to form yield a gel. The same can be done with HA or other mineral particles incorporated in the first step (low pH). Upon gelation the particles get trapped in the gel.

Example 3

In Vitro Biomineralization

In vitro biomineralization was performed with monolayer peptide films deposited on SBF1.5 solution (×1.5 ionic profile of blood serum Tris buffered to pH 7.35; Na+213.0, K+7.5, Ca+2 3.8, Mg+2 2.3, HCO3–6.3, Cl–223.0, HPO4–1.5, SO4–2 0.75 mM). Mineralization was also obtained on hydrogels that were in contact with SBF1.5 solution.

A considerable amount of work has been done in-vitro in order to decide whether acidic amino acids are indeed effective in HA formation. Usually these studies are done by exposure of surface active material to ionic solution followed by evaluation of HA nucleation degree on this surface. Ionic solutions, in which nucleation occurs, have a few variables such as, minerals components and their concentrations, buffer capacities, pH, temperature and preparation procedures. The two essential components of SBF1.5 are calcium and phosphate. The solution was prepared according to the prototype-SBF procedure developed by Kokubo (1990).

Simulated Body Fluid (SBF): The SBF consists of ion concentrations (Na+142.0 nM, K+5.0 mM, $Mg^{2+}$ 1.5 mM, $Ca^{2+}$ 2.5 mM, Cl–147.8 mM, HCO3–4.2 mM, $HPO_4^{2-}$ 1.0 mM, and $SO_4^{2-}$ 0.5 mM) similar to those of human blood plasma. However there are different versions of SBF as well as differences in saturation degrees. In one non-limiting example, reagent grade NaCl, $NaHCO_3$, KCl, $K_2HPO_4$, $MgCl_2$, $CaCl_2$ and $Na_2SO_4$ are dissolved in $ddH_2O$. Next about ~50 ml of 1M HCl are added to the solution in order to prevent the precipitation of the next added salt, $CaCl_2$. After the addition of all the salts, the pH of the solution was adjusted to ~7.35 by adding Trizma base (6 mM) and HCl at 37° C.

Example 4

In Vivo Biomineralization

A peptide matrix is prepared according to example 2 above. The matrix will be injected into a defect created in a bone of an animal. The peptide is delivered as a gel or gel with TCP or HA particulates.

Example 5

Cell Proliferation Assay

The proliferation of osteoblasts on an implant prepared according to Example 3 is tested. Proliferation is observed using PCNA staining or $^3$H-thymidine uptake. In one experiment, human osteoblasts ($10^4$-$10^6$ cells/100 ul) are grown on implants in microwell plates.

Example 6

Rat Tibia Model

Objectives: To investigate bone growth using the peptides and peptide matrices of the invention. In some examples the peptide was compared to a commercially available peptide or bone filler.
Surgical procedure: Animals are anesthetized according to standard procedure using intramuscular (IM) injection of ketamine/hyaline solution.
A bone defect is created in the proximal tibial metaphysis, 3-4 mm below the collateral ligament insertion, by drilling a hole of 2 mm diameter and 2-3 mm deep or by cutting a wedge of approximately 1.5 mm deep and 3 mm wide.
The defect is treated locally administering various amounts of a composition comprising a wetted powdered form of the peptide or a gel composition of the peptide a 1 ml syringe.
Evaluation: at the end of 6-8 weeks rats are sacrificed and the defect area evaluated histologically for gross cell morphology, cell abundance and the appearance of extra-cellular material. Standard histological staining methods are used (H&E) and the tissue samples are scored by a pathologist for evaluation of histological changes during the healing process.

Example 7

Rat Calvarial Model

Two rat calvarial defect models are used to determine the efficacy of the peptides and peptide matrices of the invention to induce bone repair of large defects. In one model, two 3 mm defects per calvaria are drilled using a trephine on both sides of the median suture; one side serves as a control. The protocol and evaluation method is described in Colombier (1999).

The second model, described in Hollinger (1990) introduces an 8 mm defect in the parietal bone. The defect is filled with the composition of the invention or an implant comprising the peptides of the invention and the incision site sutured. Following 4-6 weeks the animals are euthanized and the defect sites recovered. Histological analysis proceeds as in example 6.

Example 8

Hydrogel Formation

Four peptides were tested for their tendency to form hydrogels as function of pH and $Ca^{+2}$ ion concentrations. The peptides are 13 amino acids long having the sequence P-Y-(Z-Y)$_n$-P, wherein n=5 and Y and Z are alternating hydrophilic (Y) and hydrophobic (Z) amino acids:
1. $P_{FD}$-13-PD(FD)$_5$P
2. $P_{FE}$-13-PE(FE)$_5$P
3. $P_{LD}$-13-PD(LD)$_5$P
4. $P_{LE}$-13-PE(LE)$_5$P The experiment goal was to find appropriate conditions for hydrogel formation at physiological pH values (~7.2) assuming that the type of amino acids in the dyads will determine the propensity of the system to form hydrogels thus the pH and the $Ca^{+2}$ ionic concentration of the system.

Figure 3:
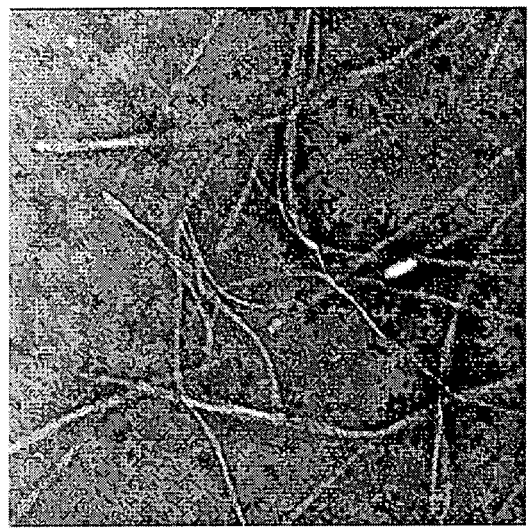
FIG. 3 represents TEM image of $P_{LD}$-13, 4% weight showing fibers of peptide which constitute a hydrogel at pH=~4.5. The fibers are typically ~10 nm in width.

In an alkaline solution the acidic amino acid side chains tend to be negatively charged. Under these conditions charge-charge repulsive forces keep the peptides dissolved in solution. Upon lowering the pH the peptides which become uncharged undergo self-assembling through inter-strand hydrogen bonding, to form fibrous structure (FIG. 3) that stabilizes highly hydrated-gel, hydrogel. Table 1 demonstrates the differences in peptide propensities towards hydrogel formation. All the peptides were dissolved in 0.1M NaOH solution (pH 13) to 4% weight per volume (w/v). All the peptides lowered the pH of the solution to about 6-8 (Table 1). Peptide $P_{LE}$-13 formed self-supporting hydrogel at neutral pH.

TABLE 1

Hydrogel formation from 4% w/v peptide dissolved in 0.1 M NaOH solution.

| Peptide name | Peptide concentration (M) | Final pH | Form of product Liquid −/gel + |
|---|---|---|---|
| $P_{LD}$-13 | 0.027 | 6 | − |
| $P_{LE}$-13 | 0.025 | 7 | + |
| $P_{FD}$-13 | 0.024 | 8 | − |
| $P_{FE}$-13 | 0.023 | 8 | − |

Two main factors appear to govern the behavior of the systems described in table 1, the differences in their molar concentrations and the type of amino acid dyads. The peptide $P_{LD}$-13 with the highest molarity (0.027M) acidified the solution down to pH~6 with no appearance of gel phase. The peptides with the lower molarity $P_{FD}$-13 (0.024M) and $P_{FE}$-13 (0.023M) dropped the pH of the NaOH solution to ~8 with no gel formation. The peptide $P_{LE}$-13 (0.025M) lowered the pH to ~7 and formed a gel. It is reasonable to assume that the lower the pH the higher the probability of the peptide to form a gel. Nevertheless, $P_{LD}$-13 (0.027M) which lowered the pH to ~6 remained fluid whereas $P_{LE}$-13 (0.025M) did assemble into a hydrogel. This difference in the behavior of the two peptides, is attributed to the higher tendency of the glutmaic acid to form inter-strand hydrogen bonds, as compared to the side chain of aspartic acid which are shorter and thus more limited in their ability to form stabilized network of hydrogen bonds. This difference between the $P_{LE}$-13 $P_{LD}$-13 behaviors demonstrates the important effect amino acids side chains may have on tuning hydrogel formation and properties. This experiment also demonstrated for the first time that PTMs may form hydrogels at physiological pH values.

Noteworthy, the pKa values of glutamic and aspartic acids are at ~4.5. Accordingly, at the pH the $P_{LE}$-13 hydrogel formed, the glutamic acid side chain should have been deprotonated. Nevertheless, it is unreasonable that a charged structure would form a stable assembly like a hydrogel. This result goes along with previously reported studies on glutamic acid rich peptides that noted a positive shift in their observed pKa values (Rapaport et al. JACS 2000 and references therein). Aspartic acid side chains probably have lower propensity towards stabilizing the beta-sheet structure therefore $P_{LD}$-13 which reduced the pH value down to ~6 did not yield a hydrogel.

The Influence of Amino Acid Hydrophobicity on Hydrogel Formation

In the next set of experiments the hypothesis that the more hydrophobic side chains would stabilize the beta-sheet fibril thus hydrogel formation, at higher pH values, was tested. Table 2 summarizes the effect of the hydrophobic side chain on the pH at which hydrogel is obtained. $P_{LE}$-13 and $P_{FE}$-13 were dissolved in different NaOH solutions to the same molar concentration (0.023M).

TABLE 2

The final pH values (+/−0.5 pH units) obtained by dissolution of 0.023 M PTMs in NaOH solution of concentrations indicated in the first column.

| NaOH M | pH | $P_{FE}$-13 | $P_{FD}$-13 | $P_{LE}$-13 | $P_{LD}$-13 |
|---|---|---|---|---|---|
| 0.01 | 12.0 | 5.5 | 5 | 5 | 4.5 |
| 0.05 | 12.7 | 6.5 | 7 | 6.5 | 5 |
| 0.07 | 12.8 | ** | 7 | 7* | 6 |
| 0.08 | 12.9 | 7.0 | 7.5 | 7 | 7.5 |
| 0.10 | 13.0 | 8.0 | 8.5 | 8 | 8.5 |

The mixtures that result in hydrogel formation are marked by gray background.
*$P_{LE}$-13 in 0.07 M NaOH gelled over night.
**There's no need to perform this experiment since the gel forms even at higher pH's.

The results of this experiment show that the peptide $P_{FE}$-13 with the more hydrophobic side chains (F) stabilized a hydrogel even at pH>7 whereas the peptide with the less hydrophobic (L) amino acid $P_{LE}$-13 requires pH~6.5 to stabilize a hydrogel. Peptide $P_{LD}$-13 forms hydrogel at lower pH compared to that of $PF_D$-13 which also forms a hydrogel, like $P_{FE}$-13, at pH~7.

The Effect of Ca+2 Ions on Hydrogel Formation

The next set of experiments (Table 3, peptide final concentration 1.34% weight) demonstrates the effect of calcium ions on the pH at which hydrogels may be obtained. With the addition of $Ca^{+2}$ ions to the solution of the peptide the system may form a hydrogel. These hydrogels are obtained at peptide concentrations smaller and at pH values higher than those without the ions. This result is explained by the stabilizing effect $Ca^{+2}$ may have on the negatively charged carboxylate groups. It is possible that the $Ca^{+2}$ may also induce cross linking between strands in a mechanism similar to that of alginate hydrogel formation. The concentration of $Ca^{+2}$ ions in the hydrogel are a few times larger than in the body serum (2.5 mM). This is envisaged to yield a better environment for the bone forming osteoblast cells. In any event, the $Ca^{+2}$ provides an additional parameter to control the hydrogel rheological and stability properties. The effect of addition of polysaccharides to the peptides on hydrogel formation is also tested to expand the hydrogel's chemical and rheological properties.

TABLE 3

The possible effect of $Ca^{+2}$ ion on the PRM hydrogel pH.

| Peptide | Conc. mM | pH mother solution | Hydrogen formation (√) upon the addition of CaCl₂ sol. $Ca^{+2}$ final concentration mM indicated | | | | |
|---|---|---|---|---|---|---|---|
| | | | 6.7 | 13.3 | 20 | 27 | 33 |
| $P_{FE}$-13 | 0.0077 | 7.5 | | | √ | √ | √ |
| $P_{FD}$-13 | 0.0081 | 7.5 | | | √ | √ | √ |
| $P_{LE}$-13 | 0.0086 | 7.2 | | | √ | √ | √ |
| $P_{LD}$-13 | 0.0091 | 7.0 | | | * | * | * |

*partial formation of hydrogel over night.

Rheology Measurements

Figure 4:
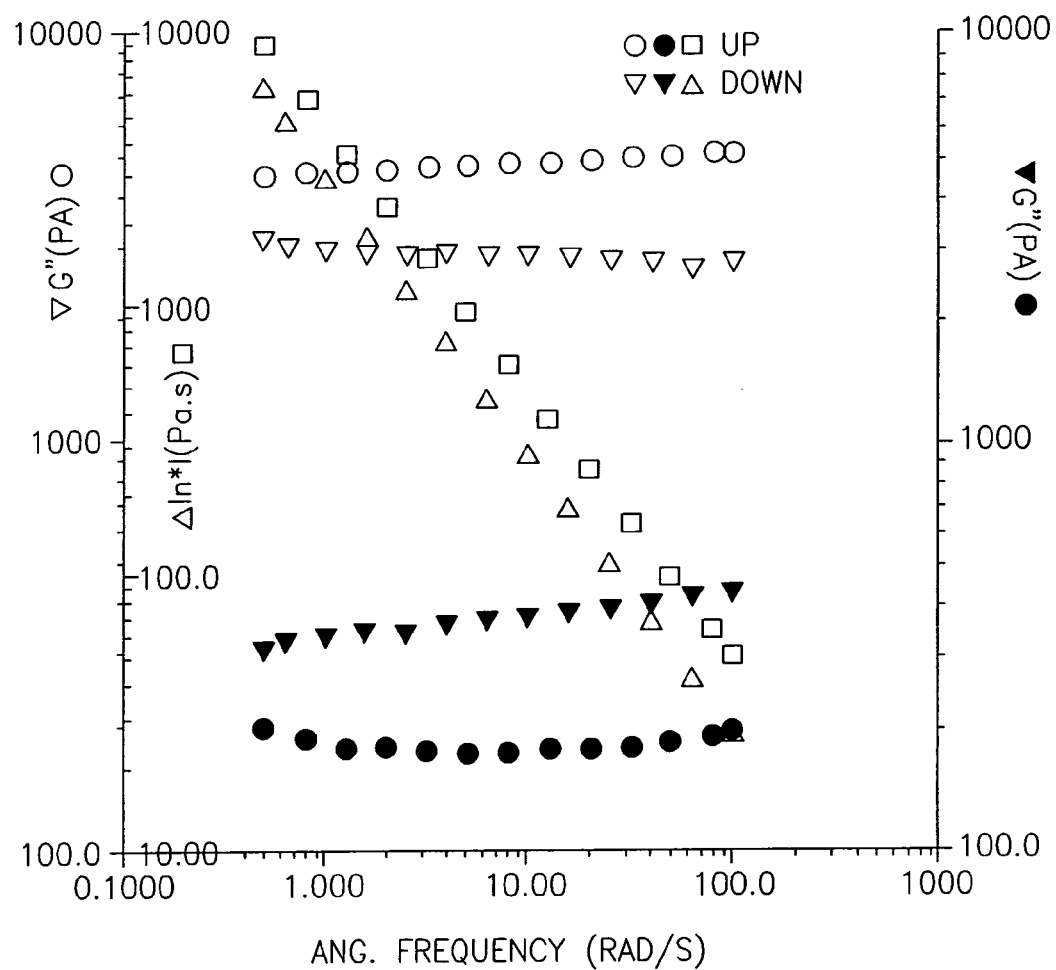
FIG. 4 describes a rheology spectra showing the storage modulus G' (open triangles and circles) and loss modulus G" (solid triangles and circles) and the steady shear viscosity study (dotted open triangles and circles) of $P_{FE}$-13 (4% w/v) hydrogel at pH=5.

The viscoelastic properties of $P_{FE}$-13 (4% w/v) hydrogel at pH=5 were measured and results are presented in FIG. 4. The high G' storage modulus value, ~3000 Pa on first sweep, indicates gel that is relatively stiff compared to that reported (~200 Pa) by Caplan et al. and within the lower range of the FMOC-dipeptides of Gazit et al. (~2000-20,000 Pa).

Forming Composite HA-PTM Hydrogels

Figure 5:
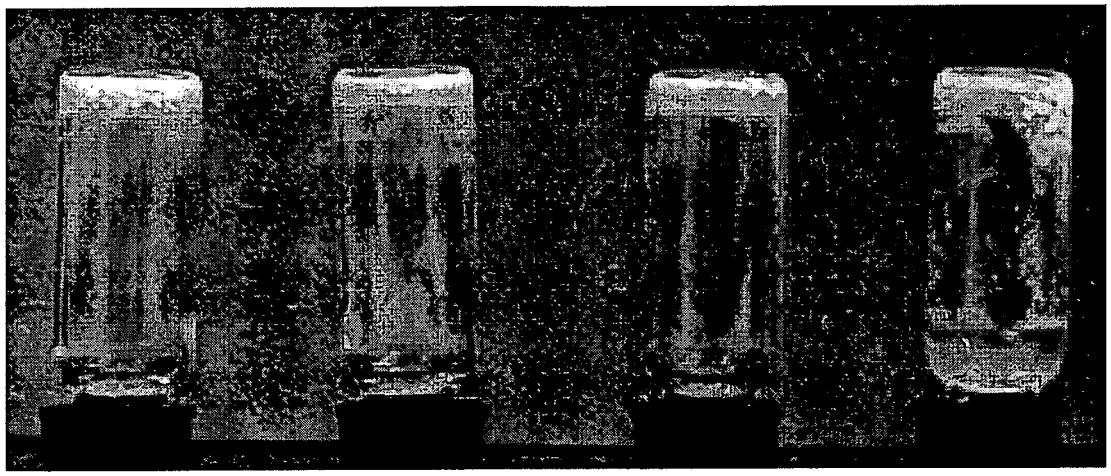
FIG. 5 depicts the $P_{FE}$-13 (4% w/v) hydrogel formed with DMEM+bicarbonate, pH~7.5 loaded with HA particles. From left to right HA concentration: 50%, 30%, 20% w/v. DMEM medium with 50% HA and no peptide did not form a hydrogel (right).

The inclusion of HA particles in hydrogels is expected to provide both a supportive environment for osteoblasts and also mechanical strength. The image in FIG. 5 demonstrates the inclusion of HA particles within $P_{FE}$-13 (2% w/v) hydrogel at pH~7

The Induction of HA Formation on Peptide Template Monolayers.

Figure 7:
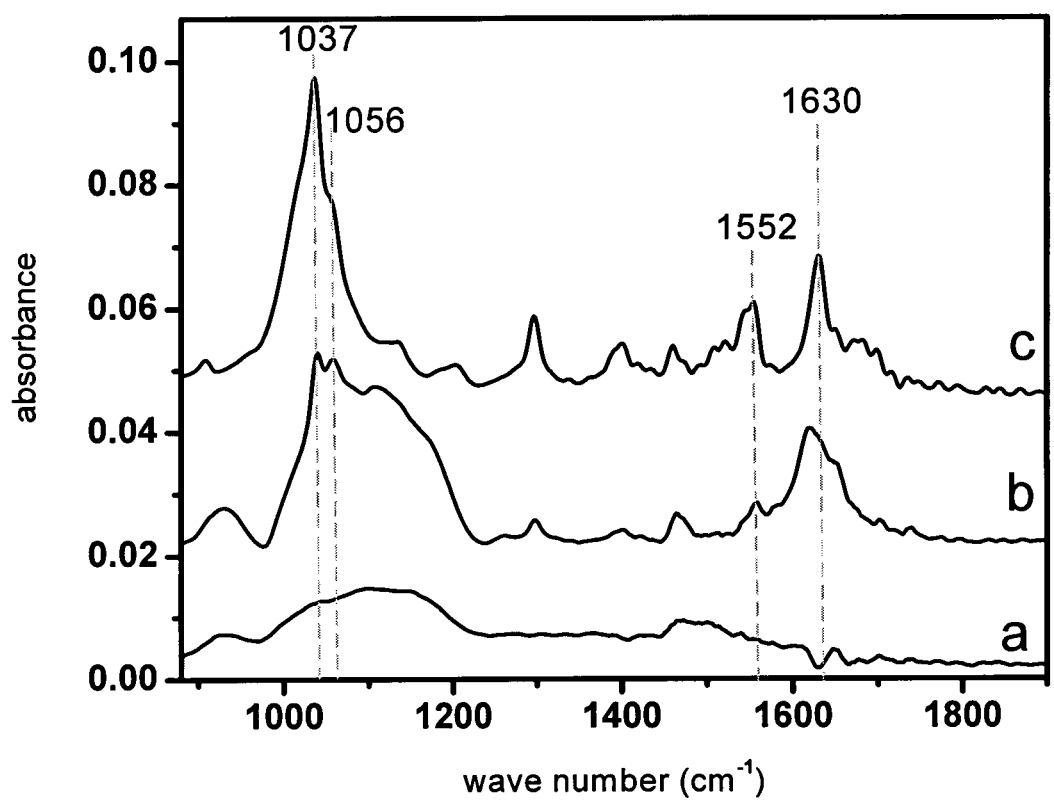
FIG. 7 is a IR spectra of a) ZnSe ATR prism soaked in $SBF_{1.5}$ for 10 days. b) peptide film that was incubated over $SBF_{1.5}$ for 10 days. c) IR spectra of the film that was incubated for 21 days. The spectra on peptide films provide a strong evidence for hydroxyapatite formation as indicated by the characteristic phosphate absorption bands at ~1037 and 1057 $cm^{-1}$, which become more intense and narrow with the incubation time.
Figure 9:
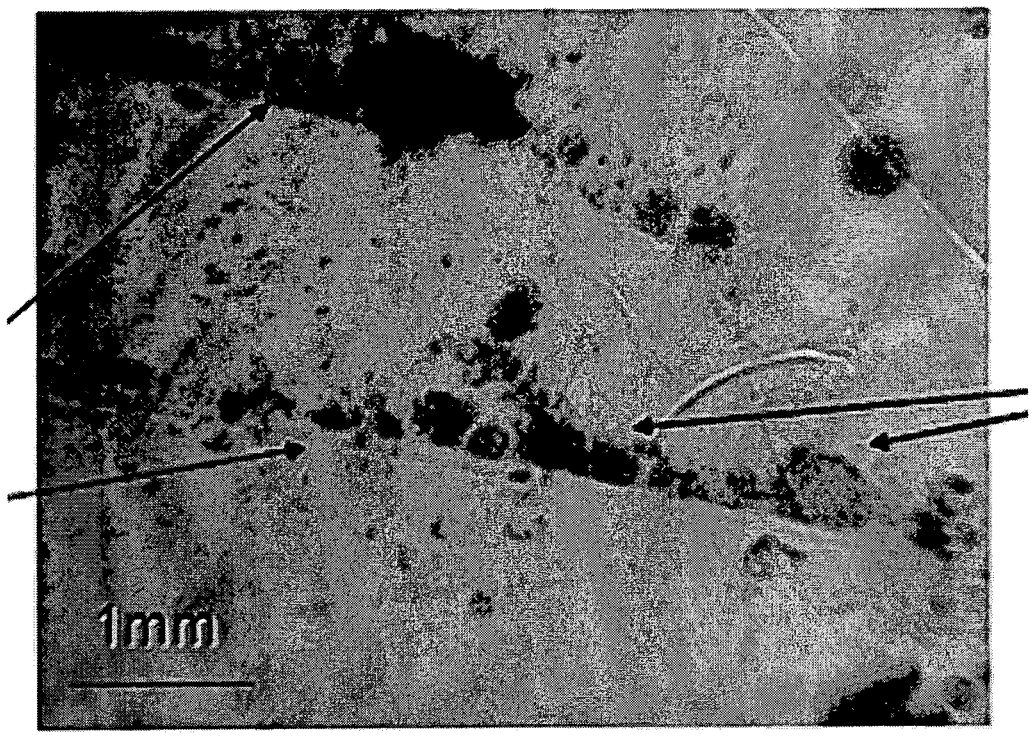
FIG. 9 represents optical phase microscope image of PFD-13 hydrogel (pH~7) that was incubated with $SBF_1$ for 21 days. The image demonstrates favorable interactions between calcium phosphate particulates (appear relatively dark, assigned by the right side arrows) and peptide hydrogel fibers (assigned by arrows pointing from the left).
Figure 10:
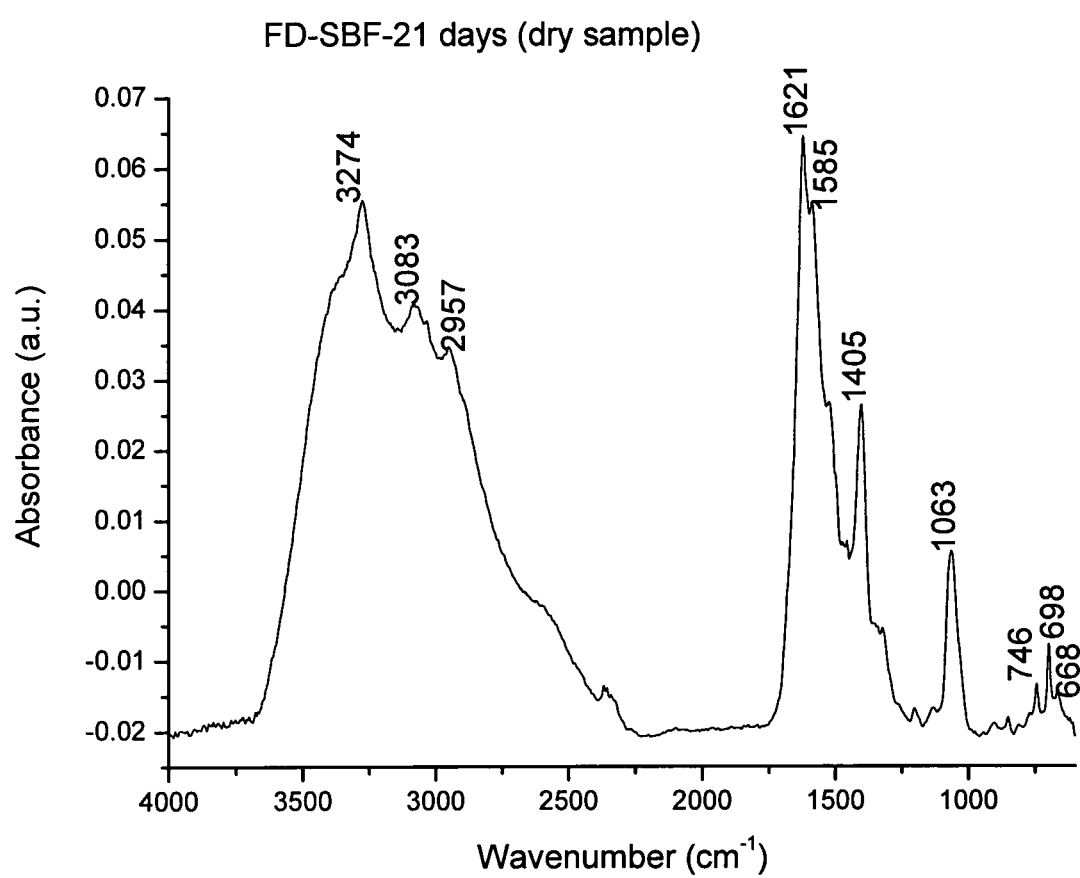
FIG. 10 presents IR spectra of the peptide $P_{FD}$-13 hydrogel/SBF1.5 sample (FIG. 9). $PO_4^{-3}$ that is the principal molecular species of apatite gives rise to absorbance in the 900-1200 $cm^{-1}$. The peak at ~1063 $cm^{-1}$ may be de-convoluted into peaks at ~1038 and ~1070 $cm^{-1}$ where the first corresponds to apatitic phosphate and the second to free phosphate.

Monolayers of peptide $P_{FD}$-13 were incubated over $SBF_{1.5}$ solution (simulated body fluid that is 1.5 times more concentrated in ion concentration compared to human blood serum). Results of Langmuir isotherms, FTIR spectra (FIG. 7) and EM images and diffraction (FIG. 6) indicate that the peptide monolayer accelerates the formation of HA compared to several controls that were tested (EM grid, ZnSe prism). The induction of HA formation is also demonstrated in the 3-D hydrogel system by optical phase microscope image (FIG. 9) and IR spectra (FIG. 10). As described in OU-YANG et al. 2000, the peak at ~1063 cm$^{-1}$ may be deconvoluted into peaks at ~1038 and ~1070 cm$^{-1}$ where the first corresponds to apatitic phosphate and the second to free phosphate.

In Vitro Cell Culturing on Hydrogels.

a. The Stability of the Hydrogels to Cell Culture Conditions

The first set of experiments examined the stability of different hydrogels to gamma irradiation (5000 rad), incubation conditions (37° C.; humidity and $CO_2$ atmosphere) and cell media addition without cells.

The hydrogels were stable to gamma irradiation and incubation conditions. As for the medium, it was rapidly taken up by the hydrogels which got swollen. The addition of liquid to the hydrogels has to be done gently as it happened that the gel disintegrated upon excessive soaking in media. The pH of the hydrogels remained stable under the experimental conditions.

b. The Human Osteosarcoma Cell Line SaOS-2 in a 2D System

The influence of the hydrogels on the adhesion, spreading and proliferation was examined on human osteosarcoma cell line SaOS-2. The in-vitro cell culture studies are performed also with endothelial cells. The cells were maintained in *Dulbecco's modified Eagle's medium (DMEM) supplemented with 10% fetal calf serum (FCS), 100 mg/ml streptomycin, 100 U/ml penicillin and 2 mmol/L L-glutamine. Cells were maintained at 37° C. in a humidified atmosphere containing 5% $CO_2$. Cell suspensions of the SaOS-2 cells were obtained after trypsin treatment. In 2D cultures the cells were seeded on top of the different hydrogels. Since the cells are almost transparent and the hydrogels are either opaque or, polarizing the light, the visualization of the cells viability under the microscope is difficult. In order to overcome this problem different cell coloring techniques, such as Tripanblue (TB); Methylen-blue (MB); Almar-blue (AB); Neutralred (NR); Hematoxylin-eosin (HE), were used. Some of the techniques were found toxic (MB, NR); others (TB, AB) did not improve visualization, and the HE technique requires fixation prior to coloring. With any of these techniques the sample is sacrificed.

The visualization of cell viability became possible using a very thin layer of hydrogel (<1 mm). The system is prepared by aliquoting 100 μl of liquid hydrogel onto a 22 mm cover slip (in a 30 mm Petri-dish). Subconfluent cells were harvested by trypsinization, counted, and diluted in the cells media to 3*10⁵ cells/ml. 50 µl of cell suspension were then pipette over the hydrogel. Cells were allowed to sit undisturbed in the incubator for 1 hr, after which 250 µl of culture media were added to the Petri-dish. Plates were then transferred to incubation for various time periods. For control uncoated cover slips were seeded in the same manner. The seeding density of SaoS$_2$ was ~3800 cells/cm$^2$ and culture medium was changed twice a week.

The results demonstrate that the hydrogels FD, FE and LE can provide a proper environment for cell adhesion spreading and proliferation (FIG. 8). Furthermore, cell division on these hydrogels has been observed.

c. Three Dimensional (3D) Cell Culture in PTM Hydrogels

In order to build a 3D system, hydrogels containing culture media were prepared. Two approaches were undertaken: first, dissolving the peptide in culture media where in order to achieve a physiological pH sodium-bicarbonate is added. Second, preparing a hydrogel with NaOH followed by lyophilization and re-wetting using a culture media. Both approaches showed positive preliminary results.

In order to evaluate quantitatively the cell viability and cell proliferation in 3D systems (especially those that including HA which cause the system to be opaque) the LIVE/DEAD Viability/Cytotoxicity Kit (Molecular Probes) is used according to the manufacture's instructions.

In-Vivo Experiments

The in-vivo tests include toxicity, biodegradation tests of hydrogels and bone augmentation studies on animal models. The effect on bone regeneration is studied on small to medium animals in holes created in bones.

The in-vivo studies include further development of the PTM-hydrogels to include:

a. Polysaccharides for improved mechanical stabilization b. Tricalcium-phosphate instead of HA that is an additional mineral used as a bone filler.

c. Additional integrin bonding motifs.

Example 9

Additional Peptides

A few more peptides were studies in order to elucidate the role of Pro termini in hydrogel formation, to test the effect of peptide length and peptide termini protecting groups. The following table summarizes the results in terms of formation of hydrogels under specific conditions, i.e. weight concentration (4% in 100 µl NaOH solution) in which peptide P$_{FD}$-13 does form hydrogel.

TABLE 4

Formation of hydrogels by additional peptides.

| peptide | NaOH conc. | Self supporting gel formation assigned + | Resultant pH |
|---|---|---|---|
| (Phe-Asp)$_6$ | 0.03 | + | ~6 |
| (Phe-Asp)$_6$ | 0.05 | + | ~7 |
| Pro-Asp-(Phe-Asp)$_6$ | 0.03 | + | ~6 |
| Pro-Asp-(Phe-Asp)$_6$ | 0.05 | + after several hrs. | ~7 |
| Ac-Pro-Asp-(Phe-Asp)$_5$-Pro-NH$_2$ | 0.03 | + | ~6 |
| Ac-Pro-Asp-(Phe-Asp)$_5$-Pro-NH$_2$ | 0.05 | Viscous liquid | >7.5 |
| Pro-Asp-Phe-Asp | 0.03 | liquid | ~3 |
| Pro-Asp-Phe-Asp | 0.05 | liquid | ~4 |

Example 10

Peptide-Polysaccharide Self-Supporting Hydrogels

Peptide polysaccharide self-supporting hydrogels were prepared by dissolving the peptide Ac-Pro-Asp-(Phe-Asp)$_5$-Pro-NH$_2$ and the polysaccharide alginate in 1:1 w/w to a final concentration of 4% in 240 µl 0.03 M NaOH, with the addition of 120 µl 0.1M CaCl$_2$ self supporting hydrogel was formed at pH ~8.5. The gel can be formed also at lower pH by dissolving the peptide/alginate mixture in NaOH of a lower pH.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

LIST OF REFERENCES

Addadi, L.; Weiner, S. Proceedings of the National Academy of Sciences of the United States of America 1985, 82, 4110-4114.

Birdi K. S., Self-assembly monolayer structures of lipids and macromolecules at interfaces. New York: Kluwer Academic/Plenum Publishers, 1999.

Bolander M E. Regulation of fracture repair by growth factors. Proc Soc Exp Biol Med. 200(2):165-70. 1992 Boskey, A. L. Journal of Cellular Biochemistry 1998, 83-91.

Caplan et al., Biomacromolecules, 2000, 1, 627 and 2001, 4, 627.

Colombier et al., Cells Tissues Organs 164:131-140, 1999.

Delange, G. L.; Donath, K. Biomaterials 1989, 10, 121-125.

DeGrado, W. F.; Lear, J. D. J. American Chemical Society 1985, 107, 7684-7689.

Ganss, B., Kim, R. H. & Sodek, J. Bone sialoprotein. *Crit. Rev. Oral. Biol. Med.* 10, 79-98 (1999).

Gilbert M, Shaw W J, Long J R, Nelson K, Drobny G P, Giachelli C M, Stayton P S. Chimeric peptides of statherin and osteopontin that bind hydroxyapatite and mediate cell adhesion. J Biol Chem. 275(21):16213-8. 2000

Goldberg H A, Warner K J, Li M C, Hunter G K. Binding of bone sialoprotein, osteopontin and synthetic polypeptides to hydroxyapatite. Connect Tissue Res.; 42(1):25-37. 2001.

He G, Gajjeraman S, Schultz D, Cookson D, Qin C, Butler W T, Hao J, George A. Spatially and temporally controlled biomineralization is facilitated by interaction between self-assembled dentin matrix protein 1 and calcium phosphate nuclei in solution. Biochemistry. 44(49):16140-8 2005.

Hollinger and Kleinschmidt, J Craniofacial Surg 1:60-68, 1990.

Hunter, G. K.; Hauschka, P. V.; Rosenberg, L. C.; Poole, A. R.; Goldberg, H. A. Journal of Dental Research 1996, 75, 913-913.

Hunter, G. K., Hauschka, P. V., Poole, A. R., Rosenberg, L. C. & Goldberg, H. A. Nucleation and inhibition of hydroxyapatite formation by mineralized tissue proteins. *Biochem. J.* 317, 59-64 (1996).

Hunziker, Osteoart. Cart., 10:432-465, 2002).

Iijima, M.; Kamemizu, H.; Wakamatsu, N.; Goto, T.; Doi, Y.; Moriwaki, Y. Journal of Crystal Growth 1998, 193, 182-188.

Koh C. J. and Atala A., 2004, J Am Soc Nephrol 15:1113-1125.

Kokubo T, Kushitani H, Sakka S, Kitsugi T, Yamamuro T Solutions able to reproduce in vivo surface-structure changes in bioactive glass-ceramic A-W. J Biomed Mater Res. 1990. 24(6):721-34.

LeGeros, R Z. Properties of osteoconductive biomaterials: calcium phosphates. Clin Orthop 395:81-98, 2002

Lowenstam, H. A. & Weiner, S. On biomineralization. (Oxford University Press, New York; 1989).

Mann, S., Biomineralization: principles and concepts in bioinorganic material chemistry. ed.; Oxford University Press: New York, 2001; 'Vol.' p.

Mann, S. Molecular recognition in biomineralization. Nature 1988, 332, 119-124.

OU-Yang et al., 2000, Two-Dimensional Vibrational Correlation Spectroscopy of In Vitro Hydroxyapatite Maturation. Biopolymers (Biospectroscopy) 57: 129-139.

Oldberg, A., Franzen, A. & Heinegard, D. The primary structure of a cell binding bone sialoprotein. *J. Biol. Chem.* 263, 19430-19432 (1988).

Oliveira, A. L.; Mano, J. F.; Reis, R. L. Current Opinion in Solid State & Materials Science 2003, 7, 309-318.

Posner, A. S. physiological reviews 1969, 49, 760-792.

Rapaport, H., Kjaer, K., Jensen, T. R., Leiserowitz, L. and Tirrell D. A., Two-Dimensional Order in β-sheet Peptide Monolayers, J. Am. Chem. Soc. 122, 12523-12529 (2000).

Rapaport, H., Möller, G., Knobler, C. M., Jensen, T. R., Kjaer, K., Leiserowitz, L. and Tirrell, D. A., Assembly of triple-stranded β-sheet peptides at interfaces, J. Am. Chem. Soc. 124, 9342-9343 (2002).

Teraub, W.; Arad, T.; Weiner, S. PNAS USA 1989, 86, 9822-9826.

Valentin, A H and Weber, J. Receptor technology-cell binding to P-15: a new method of regenerating bone quickly and safely—preliminary histomorphometrical and mechanical results in sinus floor augmentations. Keio J Med. 53(3): 166-71. 2004.

Weiner, S., Addadi, L. Journal of Materials Chemistry 1997, 7, 689-702.

Young, M. F., Kerr, J. M., Ibaraki, K., Heegaard, A.-M & Robey, P. G. Structure, expression and regulation of the major noncollagenous matrix proteins of bone. *Clin. Orthop.* 281, 275-294 (1992).

---

The invention claimed is:

1. A hydrogel composition comprising an amphiphilic peptide having the amino acid sequence selected from the group consisting of:

Pro-Glu-(Leu-Glu)5-Pro;   (SEQ ID NO: 6)

Pro-Asp-(Leu-Asp)5-Pro;   (SEQ ID NO: 7) and

Pro-Asp-(Phe-Asp)5-Pro.   (SEQ ID NO: 22)

2. The hydrogel composition of claim 1 wherein the peptide has the amino acid sequence Pro-Glu-(Leu-Glu)5-Pro (SEQ ID NO:6).

3. The hydrogel composition of claim 1 wherein the peptide has the amino acid sequence Pro-Asp-(Leu-Asp)5-Pro (SEQ ID NO:7).

4. The hydrogel composition of claim 1 wherein the peptide has the amino acid sequence Pro-Asp-(Phe-Asp)5-Pro (SEQ ID NO:22).

5. The hydrogel composition of claim 1 comprising one or more of a pre-loaded mineral-salt solution or aggregate or a pre-loaded polysaccharide.

6. The hydrogel composition of claim 5 wherein the pre-loaded mineral salt is a calcium phosphate mineral selected from the group consisting of amorphous calcium phosphate, tricalcium phosphate and hydroxyapatite or the pre-loaded polysaccharide is selected from the group consisting of hyaluronic acid, alginate and sulfated polysaccharide.

7. A pharmaceutical composition comprising at least one amphiphilic peptide according to claim 1 and a pharmaceutically acceptable carrier or excipient.

8. An implant comprising a hydrogel composition according to claim 7 and optionally further comprising a metal structure.

9. The implant of claim 8 wherein the hydrogel further comprises at least one mineral or at least one polysaccharide.

10. The implant of claim 9 wherein the mineral is a calcium phosphate mineral selected from the group consisting of amorphous calcium phosphate, tricalcium phosphate and hydroxyapatite or the polysaccharide is selected from the group consisting of hyaluronic acid, alginate and sulfated polysaccharide.

11. A method for preparing a hydrogel composition according to claim 1 which comprises:
   providing a liquid solution comprising at least one amphiphilic peptide according to claim 1 in a vessel;
   providing a solution comprising ionic calcium, optionally further comprising a therapeutic agent;
   mixing together the peptide composition and the solution;
   allowing the mixture to form a hydrogel; and
   separating a peptide/precipitate solid composition from the solution.

12. The method of claim 11 wherein the ionic calcium is selected from the group consisting of calcium chloride salt, phosphate salt, particles or particulates of calcium phosphate mineral, tricalcium phosphate and hydroxyapatite.

13. The method of claim 11 wherein the peptide is provided in powder form and the solution is an alkaline solution.

14. A kit comprising at least one amphiphilic peptide according to claim 1 and optionally further comprising a pharmaceutically acceptable carrier or excipient and an optional means for delivery of the peptide or peptide and carrier or excipient.

* * * * *

UNITED STATES PATENT AND TRADEMARK OFFICE
CERTIFICATE OF CORRECTION

PATENT NO.          : 8,658,763 B2                                                     Page 1 of 1
APPLICATION NO.  : 12/305588
DATED                  : February 25, 2014
INVENTOR(S)         : Hanna Rapaport It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1281 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 23

<210> SEQ ID NO 1
<211> LENGTH: 12
<212> TYPE: PRT
<213> ORGANISM: Artificial sequence
<220> FEATURE:
<223> OTHER INFORMATION: Synthetic peptide

<400> SEQUENCE: 1

Pro Glu Phe Glu Phe Glu Phe Glu Phe Glu Phe Glu
1               5                   10

<210> SEQ ID NO 2
<211> LENGTH: 12
<212> TYPE: PRT
<213> ORGANISM: Artificial sequence
<220> FEATURE:
<223> OTHER INFORMATION: Synthetic peptide

<400> SEQUENCE: 2

Glu Phe Glu Phe Glu Phe Glu Phe Glu Phe Glu Pro
1               5                   10

<210> SEQ ID NO 3
<211> LENGTH: 13
<212> TYPE: PRT
<213> ORGANISM: Artificial sequence
<220> FEATURE:
<223> OTHER INFORMATION: Synthetic peptide

<400> SEQUENCE: 3

Pro Ser Phe Ser Phe Ser Phe Ser Phe Ser Phe Ser Pro
1               5                   10

<210> SEQ ID NO 4
<211> LENGTH: 13
<212> TYPE: PRT
<213> ORGANISM: Artificial sequence
<220> FEATURE:
```

```
<223> OTHER INFORMATION: Synthetic peptide
<220> FEATURE:
<221> NAME/KEY: misc_feature
<222> LOCATION: (2)..(2)
<223> OTHER INFORMATION: PHOSPHORYLATION
<220> FEATURE:
<221> NAME/KEY: misc_feature
<222> LOCATION: (4)..(4)
<223> OTHER INFORMATION: PHOSPHORYLATION
<220> FEATURE:
<221> NAME/KEY: misc_feature
<222> LOCATION: (6)..(6)
<223> OTHER INFORMATION: PHOSPHORYLATION
<220> FEATURE:
<221> NAME/KEY: misc_feature
<222> LOCATION: (8)..(8)
<223> OTHER INFORMATION: PHOSPHORYLATION
<220> FEATURE:
<221> NAME/KEY: misc_feature
<222> LOCATION: (10)..(10)
<223> OTHER INFORMATION: PHOSPHORYLATION
<220> FEATURE:
<221> NAME/KEY: misc_feature
<222> LOCATION: (12)..(12)
<223> OTHER INFORMATION: PHOSPHORYLATION

<400> SEQUENCE: 4

Pro Ser Phe Ser Phe Ser Phe Ser Phe Ser Phe Ser Pro
1               5                   10

<210> SEQ ID NO 5
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: PHOSPHORYLATION
<220> FEATURE:
<221> NAME/KEY: misc_feature
<222> LOCATION: (4)..(4)
<223> OTHER INFORMATION: PHOSPHORYLATION
<220> FEATURE:
<221> NAME/KEY: misc_feature
<222> LOCATION: (6)..(6)
<223> OTHER INFORMATION: PHOSPHORYLATION
<220> FEATURE:
<221> NAME/KEY: misc_feature
<222> LOCATION: (8)..(8)
<223> OTHER INFORMATION: PHOSPHORYLATION
<220> FEATURE:
<221> NAME/KEY: misc_feature
<222> LOCATION: (10)..(10)
<223> OTHER INFORMATION: PHOSPHORYLATION
<220> FEATURE:
<221> NAME/KEY: misc_feature
<222> LOCATION: (12)..(12)
<223> OTHER INFORMATION: PHOSPHORYLATION

<400> SEQUENCE: 5

Pro Tyr Phe Tyr Phe Tyr Phe Tyr Phe Tyr Phe Tyr Pro
1               5                   10

<210> SEQ ID NO 6
<211> LENGTH: 13
<212> TYPE: PRT
<213> ORGANISM: Artificial sequence
<220> FEATURE:
<223> OTHER INFORMATION: Synthetic peptide

<400> SEQUENCE: 6

Pro Glu Leu Glu Leu Glu Leu Glu Leu Glu Leu Glu Pro
1               5                   10
```

```
<210> SEQ ID NO 7
<211> LENGTH: 13
<212> TYPE: PRT
<213> ORGANISM: Artificial sequence
<220> FEATURE:
<223> OTHER INFORMATION: Synthetic peptide

<400> SEQUENCE: 7

Pro Asp Leu Asp Leu Asp Leu Asp Leu Asp Leu Asp Pro
1               5                   10

<210> SEQ ID NO 8
<211> LENGTH: 13
<212> TYPE: PRT
<213> ORGANISM: Artificial sequence
<220> FEATURE:
<223> OTHER INFORMATION: Synthetic peptide

<400> SEQUENCE: 8

Pro Ser Leu Ser Leu Ser Leu Ser Leu Ser Leu Ser Pro
1               5                   10

<210> SEQ ID NO 9
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: PHOSPHORYLATION
<220> FEATURE:
<221> NAME/KEY: misc_feature
<222> LOCATION: (4)..(4)
<223> OTHER INFORMATION: PHOSPHORYLATION
<220> FEATURE:
<221> NAME/KEY: misc_feature
<222> LOCATION: (6)..(6)
<223> OTHER INFORMATION: PHOSPHORYLATION
<220> FEATURE:
<221> NAME/KEY: misc_feature
<222> LOCATION: (8)..(8)
<223> OTHER INFORMATION: PHOSPHORYLATION
<220> FEATURE:
<221> NAME/KEY: misc_feature
<222> LOCATION: (10)..(10)
<223> OTHER INFORMATION: PHOSPHORYLATION
<220> FEATURE:
<221> NAME/KEY: misc_feature
<222> LOCATION: (12)..(12)
<223> OTHER INFORMATION: PHOSPHORYLATION

<400> SEQUENCE: 9

Pro Ser Leu Ser Leu Ser Leu Ser Leu Ser Leu Ser Pro
1               5                   10

<210> SEQ ID NO 10
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: PHOSPHORYLATION
<220> FEATURE:
<221> NAME/KEY: misc_feature
<222> LOCATION: (4)..(4)
<223> OTHER INFORMATION: PHOSPHORYLATION
<220> FEATURE:
```

```
<221> NAME/KEY: misc_feature
<222> LOCATION: (6)..(6)
<223> OTHER INFORMATION: PHOSPHORYLATION
<220> FEATURE:
<221> NAME/KEY: misc_feature
<222> LOCATION: (8)..(8)
<223> OTHER INFORMATION: PHOSPHORYLATION
<220> FEATURE:
<221> NAME/KEY: misc_feature
<222> LOCATION: (10)..(10)
<223> OTHER INFORMATION: PHOSPHORYLATION
<220> FEATURE:
<221> NAME/KEY: misc_feature
<222> LOCATION: (12)..(12)
<223> OTHER INFORMATION: PHOSPHORYLATION

<400> SEQUENCE: 10

Pro Tyr Leu Tyr Leu Tyr Leu Tyr Leu Tyr Leu Tyr Pro
1               5                   10

<210> SEQ ID NO 11
<211> LENGTH: 19
<212> TYPE: PRT
<213> ORGANISM: Artificial sequence
<220> FEATURE:
<223> OTHER INFORMATION: Synthetic peptide

<400> SEQUENCE: 11

Pro Glu Phe Ser Phe Glu Phe Ser Phe Glu Phe Ser Phe Glu Phe Ser
1               5                   10                  15

Phe Glu Pro

<210> SEQ ID NO 12
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: PHOSPHORYLATION
<220> FEATURE:
<221> NAME/KEY: misc_feature
<222> LOCATION: (6)..(6)
<223> OTHER INFORMATION: PHOSPHORYLATION
<220> FEATURE:
<221> NAME/KEY: misc_feature
<222> LOCATION: (10)..(10)
<223> OTHER INFORMATION: PHOSPHORYLATION
<220> FEATURE:
<221> NAME/KEY: misc_feature
<222> LOCATION: (14)..(14)
<223> OTHER INFORMATION: PHOSPHORYLATION

<400> SEQUENCE: 12

Pro Ser Phe Ser Phe Ser Phe Ser Phe Ser Phe Ser Phe Ser Phe Ser
1               5                   10                  15

Phe Ser Pro

<210> SEQ ID NO 13
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: PHOSPHORYLATION
<220> FEATURE:
<221> NAME/KEY: misc_feature
```

```
<222> LOCATION: (6)..(6)
<223> OTHER INFORMATION: PHOSPHORYLATION
<220> FEATURE:
<221> NAME/KEY: misc_feature
<222> LOCATION: (10)..(10)
<223> OTHER INFORMATION: PHOSPHORYLATION
<220> FEATURE:
<221> NAME/KEY: misc_feature
<222> LOCATION: (14)..(14)
<223> OTHER INFORMATION: PHOSPHORYLATION

<400> SEQUENCE: 13

Pro Ser Phe Glu Phe Ser Phe Glu Phe Ser Phe Glu Phe Ser Phe Glu
1               5                   10                  15

Phe Glu Pro

<210> SEQ ID NO 14
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: PHOSPHORYLATION
<220> FEATURE:
<221> NAME/KEY: misc_feature
<222> LOCATION: (6)..(6)
<223> OTHER INFORMATION: PHOSPHORYLATION
<220> FEATURE:
<221> NAME/KEY: misc_feature
<222> LOCATION: (10)..(10)
<223> OTHER INFORMATION: PHOSPHORYLATION
<220> FEATURE:
<221> NAME/KEY: misc_feature
<222> LOCATION: (14)..(14)
<223> OTHER INFORMATION: PHOSPHORYLATION

<400> SEQUENCE: 14

Pro Ser Phe Asp Phe Ser Phe Asp Phe Ser Phe Asp Phe Ser Phe Asp
1               5                   10                  15

Phe Asp Pro

<210> SEQ ID NO 15
<211> LENGTH: 30
<212> TYPE: PRT
<213> ORGANISM: Artificial sequence
<220> FEATURE:
<223> OTHER INFORMATION: Synthetic peptide

<400> SEQUENCE: 15

Ala Leu Glu Phe Glu Phe Glu Phe Glu Pro Ala Glu Phe Glu Phe Glu
1               5                   10                  15

Phe Glu Leu Pro Ala Leu Glu Phe Glu Phe Glu Phe Glu Pro
            20                  25                  30

<210> SEQ ID NO 16
<211> LENGTH: 13
<212> TYPE: PRT
<213> ORGANISM: Artificial sequence
<220> FEATURE:
<223> OTHER INFORMATION: Synthetic peptide

<400> SEQUENCE: 16

Pro Glu Phe Glu Phe Glu Lys Glu Phe Glu Phe Glu Pro
1               5                   10

<210> SEQ ID NO 17
```

```
<211> LENGTH: 19
<212> TYPE: PRT
<213> ORGANISM: Artificial sequence
<220> FEATURE:
<223> OTHER INFORMATION: Synthetic peptide

<400> SEQUENCE: 17

Pro Glu Phe Glu Phe Glu Phe Glu Phe Glu Phe Glu Gly Gly Gly Arg
1               5                   10                  15

Gly Asp Ser

<210> SEQ ID NO 18
<211> LENGTH: 14
<212> TYPE: PRT
<213> ORGANISM: Artificial sequence
<220> FEATURE:
<223> OTHER INFORMATION: Synthetic peptide

<400> SEQUENCE: 18

Phe Glu Phe Glu Phe Glu Pro Gly Gly Gly Arg Gly Asp Ser
1               5                   10

<210> SEQ ID NO 19
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: ACETYLATION
<220> FEATURE:
<221> NAME/KEY: misc_feature
<222> LOCATION: (13)..(13)
<223> OTHER INFORMATION: AMIDATION

<400> SEQUENCE: 19

Pro Asp Phe Asp Phe Asp Phe Asp Phe Asp Phe Asp Pro
1               5                   10

<210> SEQ ID NO 20
<211> LENGTH: 14
<212> TYPE: PRT
<213> ORGANISM: Artificial sequence
<220> FEATURE:
<223> OTHER INFORMATION: Synthetic peptide

<400> SEQUENCE: 20

Pro Asp Phe Asp Phe Asp Phe Asp Phe Asp Phe Asp Phe Asp
1               5                   10

<210> SEQ ID NO 21
<211> LENGTH: 12
<212> TYPE: PRT
<213> ORGANISM: Artificial sequence
<220> FEATURE:
<223> OTHER INFORMATION: Synthetic peptide

<400> SEQUENCE: 21

Phe Asp Phe Asp Phe Asp Phe Asp Phe Asp Phe Asp
1               5                   10

<210> SEQ ID NO 22
<211> LENGTH: 13
<212> TYPE: PRT
<213> ORGANISM: Artificial sequence
<220> FEATURE:
<223> OTHER INFORMATION: Synthetic peptide
```

```
<400> SEQUENCE: 22

Pro Asp Phe Asp Phe Asp Phe Asp Phe Asp Phe Asp Pro
1               5                   10

<210> SEQ ID NO 23
<211> LENGTH: 13
<212> TYPE: PRT
<213> ORGANISM: Artifical sequence
<220> FEATURE:
<223> OTHER INFORMATION: Synthetic peptide

<400> SEQUENCE: 23

Pro Glu Phe Glu Phe Glu Phe Glu Phe Glu Phe Glu Pro
1               5                   10
```